United States Patent
Gebert et al.

(10) Patent No.: US 9,132,073 B2
(45) Date of Patent: Sep. 15, 2015

(54) OXIDATION DYE PRECURSORS

(71) Applicant: Henkel AG & Co. KGaA, Dusseldorf (DE)

(72) Inventors: Antje Gebert, Duesseldorf (DE); Annika Koenen, Grevenbroich (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 14/465,937

(22) Filed: Aug. 22, 2014

(65) Prior Publication Data

US 2014/0359951 A1    Dec. 11, 2014

Related U.S. Application Data

(63) Continuation of application No. PCT/EP2013/053470, filed on Feb. 21, 2013.

(30) Foreign Application Priority Data

Feb. 23, 2012    (DE) .......... 10 2012 202 782

(51) Int. Cl.
| | |
|---|---|
| *A61Q 5/10* | (2006.01) |
| *C07D 327/10* | (2006.01) |
| *A61K 8/49* | (2006.01) |
| *C07D 319/20* | (2006.01) |
| *C07D 327/06* | (2006.01) |
| *C07D 241/42* | (2006.01) |
| *C07D 241/44* | (2006.01) |

(52) U.S. Cl.
CPC . *A61K 8/49* (2013.01); *A61K 8/494* (2013.01); *A61K 8/498* (2013.01); *A61K 8/4913* (2013.01); *A61K 8/4953* (2013.01); *A61Q 5/10* (2013.01); *C07D 241/42* (2013.01); *C07D 241/44* (2013.01); *C07D 319/20* (2013.01); *C07D 327/06* (2013.01); *A61K 2800/10* (2013.01)

(58) Field of Classification Search
CPC ...... A61Q 5/10; C07D 327/06; C07D 319/20; C07D 241/42; C07D 241/44; A61K 8/49; A61K 8/498; A61K 8/4913; A61K 8/4953; A61K 8/494; A61K 2800/10
USPC ........................................ 8/406; 549/15, 366
See application file for complete search history.

(56) References Cited

U.S. PATENT DOCUMENTS 7,396,369 B2 *    7/2008   Ramos-Stanbury ............. 8/405

FOREIGN PATENT DOCUMENTS

| DE | 3913477 A1 | 10/1990 |
|---|---|---|
| DE | 102004039357 A1 | 3/2006 |
| WO | 90/12562 A1 | 11/1990 |

OTHER PUBLICATIONS

STIC Search Report dated Oct. 7, 2014.*
PCT International Search Report (PCT/EP2013/053470) dated Jul. 21, 2014.

* cited by examiner

*Primary Examiner* — Eisa Elhilo
(74) *Attorney, Agent, or Firm* — David K. Benson

(57) ABSTRACT

An agent for oxidative coloring of keratin-containing fibers, in particular human hair, includes as oxidation dye precursor of the developer type at least one compound of formula (I).

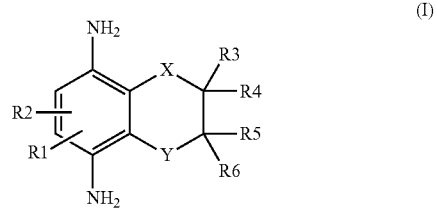

(I)

18 Claims, No Drawings

OXIDATION DYE PRECURSORS

FIELD OF THE INVENTION

The present invention generally relates to an agent for oxidative color modification of keratin-containing fibers, in particular human hair, which includes specific anellated p-phenylenediamine derivatives, to the use of these agents as color modifying agents for keratin-containing fibers for improving coloring results and to a method for coloring keratin-containing fibers, in particular human hair.

BACKGROUND OF THE INVENTION

Modifying the shape and color of hair is an important area of modern cosmetics. Consumers make use of color-modifying agents to obtain fashionable coloring of hairstyles or to conceal grayed or even white hair with fashionable or natural color shades.

Depending on the requirements placed on the coloring or color modification, a person skilled in the art is aware of various systems for providing color-modifying cosmetic agents, in particular for the skin or keratin-containing fibers such as for example human hair.

"Oxidation coloring agents" are used to achieve permanent, intense colorings with corresponding fastness properties. Such coloring agents conventionally include oxidation dye precursors, i.e. "developer components" and "coupler components". Under the influence of oxidizing agents or of atmospheric oxygen, the developer components develop the actual dyes through action with one another or through coupling with one or more coupler components. Oxidation coloring agents are distinguished by intense, excellent and long-lasting coloring results. A mixture of a relatively large number of oxidation dye precursors must, however, normally be used if natural looking colorings are to be obtained; furthermore in many cases, substantive dyes are additionally used for shading purposes. Despite their advantageous coloring characteristics, oxidative hair coloring agents are associated with disadvantages for users. In particular, it is suspected that some common oxidation dye precursors, including p-phenylenediamine, have an irritant action on some consumers and consequently cause sensitization or even allergic reactions. There is therefore still a requirement to achieve further improvements in these substances with regard to their physiological acceptability profile. Numerous compounds have been researched during the search for replacement substances, but many suffer from applicational problems, in particular inadequate gray coverage capacity. Moreover, despite highly sophisticated coloring systems already having been developed, there is still a need for coloring systems which achieve excellent luminosity and intensity of the colorings while also having a very good durability and excellent homogeneity.

It is therefore desirable to reduce the above-stated disadvantages of oxidative hair coloring agents, and to provide coloring agents that impart to the hair intense colorings with elevated colorfulness and with good resistance to external influences, in particular with good light fastness and washing fastness, which do not suffer from color attenuation or color shifts even after repeated shampooing of the hair. It is further desirable that colorings should have the least possible selectivity, i.e. achieve maximally homogeneous and uniform coloring results on differently pretreated hair. The coloring agents should moreover have a toxicologically advantageous profile.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

An agent for oxidative color modification of keratinic fibers, characterized in that it includes in a cosmetic carrier as oxidation dye precursor of the developer type at least one compound of formula (I)

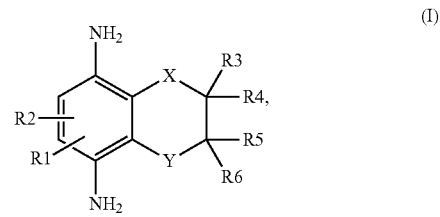

in which R1 and R2 mutually independently denote a hydrogen atom, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom; R3, R4, R5, R6 in each case mutually independently denote a hydrogen atom, a $C_1$-$C_6$ alkyl group, a $C_2$-$C_6$ alkenyl group, a $C_1$-$C_6$ hydroxyalkyl group, a $C_1$-$C_6$ alkoxy group, an amino group, a $C_1$-$C_6$ alkylamino group, a di($C_1$-$C_6$-alkyl)amino group, an N-(azacycloalkyl) group, an amino-($C_1$-$C_6$)-alkyl group, a $C_1$-$C_6$-alkylamino-$C_1$-$C_6$-alkyl group, a di-$C_1$-$C_6$-alkylamino-$C_1$-$C_6$-alkyl group, an N-(azacycloalkyl)-$C_1$-$C_6$-alkyl group, a $C_2$-$C_6$ polyhydroxyalkyl group, an acetoxy-$C_1$-$C_6$-alkyl group, a $C_1$-$C_6$-alkoxy-$C_1$-$C_6$-alkyl group, a carboxy-$C_1$-$C_6$-alkyl group or a halogen atom; X and Y in each case mutually independently denote oxygen, sulfur, a group N—R7 or methylene; R7 denotes a hydrogen atom, a $C_1$-$C_6$ alkyl group, a $C_2$-$C_6$ alkenyl group, a $C_1$-$C_6$ hydroxyalkyl group or a $C_2$-$C_6$ polyhydroxyalkyl group, with the proviso that, if X and Y in each case denote oxygen, then R1 and R2 mutually independently denote hydrogen or methoxy; and that, if X and Y in each case denote oxygen and R1 and R2 in each case denote hydrogen, then at least one of the residues R3, R4, R5 and/or R6 denotes an amino-($C_1$-$C_6$)-alkyl group, a $C_1$-$C_6$-alkylamino-$C_1$-$C_6$-alkyl group, a di($C_1$-$C_6$-alkyl) amino-$C_1$-$C_6$-alkyl group or an N-(azacycloalkyl)-$C_1$-$C_6$-alkyl group; and/or the physiologically acceptable salt thereof.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has now been found that specific anellated p-phenylenediamine derivatives are outstandingly suitable as oxidation dye precursors for coloring keratin-containing fibers. They provide coloring results with elevated color intensity and excellent brightness together with excellent gray coverage.

Anellated p-phenylenediamines in the form of unsubstituted 5,8-diaminobenzo-1,4-dioxanes are known from DE 3913477.

The present invention accordingly firstly provides an agent for oxidative color modification of keratinic fibers which is characterized in that it includes in a cosmetic carrier as oxidation dye precursor of the developer type at least one compound of formula (I)

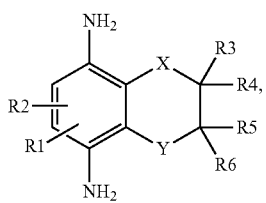

in which
R1 and R2 mutually independently denote a hydrogen atom, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom,
R3, R4, R5, R6 in each case mutually independently denote a hydrogen atom, a $C_1$-$C_6$ alkyl group, a $C_2$-$C_6$ alkenyl group, a $C_1$-$C_6$ hydroxyalkyl group, a $C_1$-$C_6$ alkoxy group, an amino group, a $C_1$-$C_6$ alkylamino group, a di($C_1$-$C_6$-alkyl)amino group, an N-(azacycloalkyl) group, an amino-($C_1$-$C_6$)-alkyl group, a $C_1$-$C_6$-alkylamino-$C_1$-$C_6$-alkyl group, a di-($C_1$-$C_6$-alkyl)amino-$C_1$-$C_6$-alkyl group, an N-(azacycloalkyl)-$C_1$-$C_6$-alkyl group, a $C_2$-$C_6$ polyhydroxyalkyl group, an acetoxy-$C_1$-$C_6$-alkyl group, a $C_1$-$C_6$-alkoxy-$C_1$-$C_6$-alkyl group, a carboxy-$C_1$-$C_6$-alkyl group or a halogen atom,
X and Y in each case mutually independently denote oxygen, sulfur, a group N—R7 or methylene,
R7 denotes a hydrogen atom, a $C_1$-$C_6$ alkyl group, a $C_2$-$C_6$ alkenyl group, a $C_1$-$C_6$ hydroxyalkyl group or a $C_2$-$C_6$ polyhydroxyalkyl group,
with the proviso that, if X and Y in each case denote oxygen, then R1 and R2 mutually independently denote hydrogen or methoxy, and that, if X and Y in each case denote oxygen and R1 and R2 in each case denote hydrogen, then at least one of the residues R3, R4, R5 and/or R6 denotes an amino-($C_1$-$C_6$)-alkyl group, a $C_1$-$C_6$-alkylamino-$C_1$-$C_6$-alkyl group, a di($C_1$-$C_6$-alkyl)amino-$C_1$-$C_6$-alkyl group or an N-(azacycloalkyl)-$C_1$-$C_6$-alkyl group, and/or the physiologically acceptable salt thereof.

Keratinic fibers should be taken to mean wool, furs, feathers and in particular human hair. The coloring agents according to the invention may however in principle also be used to color other natural fibers, such as for example cotton, jute, sisal, linen or silk, modified natural fibers, such as for example regenerated cellulose, nitro-, alkyl- or hydroxyalkylcellulose or cellulose acetate.

The agents according to the invention include the compounds of formula (I) in a cosmetic carrier, preferably in a suitable aqueous, alcoholic or aqueous-alcoholic carrier. Carriers suitable for the purpose of hair coloring are for example creams, emulsions, gels or also surfactant-containing foaming solutions, such as for example shampoos, mousse aerosols, mousse formulations or other preparations which are suitable for use on the hair. It is also feasible, however, to incorporate the dye intermediates according to formula (I) into a pulverulent or also tablet-form formulation.

For the purposes of the present invention, aqueous-alcoholic solutions should be taken to be aqueous solutions including 3 to 70 wt. % of a $C_1$-$C_4$ alcohol, in particular ethanol or isopropanol. The agents according to the invention may additionally include further organic solvents, such as for example methoxybutanol, benzyl alcohol, ethyl diglycol or 1,2-propylene glycol. Any water-soluble organic solvents are here preferred. Examples of the substituents R1, R2 and R3, R4, R5 and R6 stated in formula (I) are here stated by way of example:

Examples of $C_1$-$C_6$ alkyl residues are —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)CH_2CH_3$, —$C(CH_3)_3$, —$(CH_2)_4$—$CH_3$, —$(CH_2)_5CH_3$. More preferred alkyl residues are methyl and ethyl. Examples of $C_2$-$C_6$ alkenyl groups are prop-2-enyl (allyl group), 2-methylprop-2-enyl, but-3-enyl, but-2-enyl, pent-4-enyl or pent-3-enyl. Examples of $C_1$-$C_6$ hydroxyalkyl groups are —$CH_2OH$, —$CH_2CH_2OH$, —$CH_2CH_2CH_2OH$, —$CH_2CH(OH)CH_3$, —$CH_2CH_2CH_2CH_2OH$, wherein —$CH_2CH_2OH$ is preferred. Examples of $C_2$-$C_6$ polyhydroxyalkyl groups are 2,3-dihydroxypropyl group, 3,4-dihydroxybutyl group, 2,4-dihydroxybutyl group and 1,2-dihydroxyethyl group. Examples of $C_1$-$C_6$ alkoxy groups are —$OCH_3$, —$OCH_2CH_3$, —$OCH_2CH_2CH_3$, —$OCH(CH_3)_2$ or —$OC(CH_3)_3$, preferably methoxy group (—$OCH_3$). Examples of $C_1$-$C_6$-alkoxy-$C_1$-$C_6$-alkyl groups are —$CH_2OCH_3$, —$CH_2OCH_2CH_3$, —$CH_2OCH(CH_3)_2$, —$CH_2CH_2OCH_3$, —$CH_2OCH_2CH_2OCH_3$, —$CH_2CH_2OCH_2CH_3$, —$CH_2CH_2CH_2OCH_2CH_3$, —$CH_2CH_2OCH(CH_3)_2$, —$CH_2CH_2CH_2OCH(CH_3)_2$. Examples of halogen are fluorine, chlorine, bromine or iodine, in particular fluorine, bromine and chlorine.

Examples of $C_1$-$C_6$ alkylamino groups are methylamino, ethylamino, 1-propylamino and 2-propylamino. Examples of di($C_1$-$C_6$-alkyl)amino groups are dimethylamino, diethylamino, and 3-dipropylamino. Examples of an N-(azacycloalkyl) group are N-pyrrolidinyl and N-piperidyl.

Examples of amino-$C_1$-$C_6$-alkyl groups are aminomethyl, 2-aminoethyl, 3-aminopropyl or 2-aminopropyl. Examples of $C_1$-$C_6$-alkylamino-$C_1$-$C_6$-alkyl groups are (methylamino)methyl, 2-(methylamino)ethyl, 3-(methylamino)propyl, (ethylamino)methyl, 2-(ethylamino)ethyl and 3-(ethylamino)propyl. Particularly suitable di($C_1$-$C_6$-alkyl)amino-$C_1$-$C_6$-alkyl groups are (dimethylamino)methyl, 2-(dimethylamino)ethyl, 3-(dimethylamino)propyl, (diethylamino)methyl, 2-(diethylamino)ethyl and 3-(diethylamino)propyl. Examples of an N-(azacycloalkyl)-$C_1$-$C_6$-alkyl group are N-pyrrolidinylmethyl, N-piperidylmethyl, 2-(N-pyrrolidinyl)ethyl and 2-(N-piperidyl)ethyl. Examples of acetoxy-$C_1$-$C_6$-alkyl groups are acetoxymethyl and 2-(acetoxy)ethyl. Examples of carboxy-$C_1$-$C_6$-alkyl groups are carboxymethyl, 2-(carboxy)ethyl and 3-(carboxy)propyl.

In one embodiment of the first subject matter of the invention, an agent according to the invention is characterized in that it includes a compound of formula (I) in which X and Y in each case denote a group N—R7, in particular a group N—H.

In a further embodiment of the first subject matter of the invention, an agent according to the invention is characterized in that it includes a compound of formula (I) in which X denotes oxygen and Y denotes sulfur.

More preferred compounds of formula (I) are those in which the residues R3, R4, R5 or R6 in each case mutually independently denote a hydrogen atom, a $C_1$-$C_6$ alkyl group, a $C_1$-$C_6$ alkoxy group, an amino group, a di($C_1$-$C_6$-alkyl) amino group, an N-(azacycloalkyl) group or a $C_1$-$C_6$-dialkylamino-$C_1$-$C_6$-alkyl group, in particular if X and Y in each case denote a group N—R7, in particular a group N—H, or if X denotes oxygen and Y denotes sulfur.

A further embodiment of the first subject matter of the invention is therefore characterized in that the agent includes a compound of formula (I) in which the residues R3, R4, R5 or R6 in each case mutually independently denote a hydrogen atom, a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group.

Particularly advantageous effects are achieved if exactly one of the substituents R3, R4, R5 and R6 does not denote a hydrogen residue.

Further preferred compounds of formula (I) are those in which X and Y in each case denote oxygen, R1 and R2 mutually independently denote hydrogen or methoxy and at least one of the residues R3, R4, R5 and/or R6 denotes a $C_1$-$C_6$-dialkylamino-$C_1$-$C_6$-alkyl group or an N-(azacycloalkyl)-$C_1$-$C_6$-alkyl group.

A further embodiment of the first subject matter of the invention is thus characterized in that the agent includes a compound of formula (I) in which X and Y in each case denote oxygen, R1 and R2 mutually independently denote hydrogen or methoxy and at least one of the residues R3, R4, R5 and/or R6 denotes a $C_1$-$C_6$-dialkylamino-$C_1$-$C_6$-alkyl group or an N-(azacycloalkyl)-$C_1$-$C_6$-alkyl group.

A further preferred embodiment of the first subject matter of the invention is characterized in that the agent includes a compound of formula (I) in which X and Y do not simultaneously denote oxygen and only one of the two residues R1 or R2 denotes hydrogen.

A further preferred embodiment of the first subject matter of the invention is characterized in that the agent includes a compound of formula (I) in which X and Y do not simultaneously denote oxygen and one of the two residues R1 or R2 denotes hydrogen and the other residue R2 or R1 denotes a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom. A further preferred embodiment of the first subject matter of the invention is characterized in that the agent includes a compound of formula (I) in which X and Y do not simultaneously denote oxygen and one of the two residues R1 or R2 denotes hydrogen and the other residue R2 or R1 denotes a methoxy group.

A further preferred embodiment of the first subject matter of the invention is characterized in that the agent includes a compound of formula (I) in which X and Y do not simultaneously denote oxygen and the two residues R1 and R2 mutually independently denote a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

A further preferred embodiment of the first subject matter of the invention is characterized in that the agent includes a compound of formula (I) in which X and Y do not simultaneously denote oxygen and the two residues R1 and R2 denote a methoxy group. A further preferred embodiment of the first subject matter of the invention is characterized in that the agent includes a compound of formula (I) in which X and Y do not simultaneously denote oxygen and exactly one of the residues R3, R4, R5 or R6 denotes a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group and the other three residues are hydrogen atoms.

A further preferred embodiment of the first subject matter of the invention is characterized in that the agent includes a compound of formula (I) in which X and Y do not simultaneously denote oxygen and exactly one of the residues R3, R4, R5 or R6 denotes a methyl group and the other three residues are hydrogen atoms.

A further preferred embodiment of the first subject matter of the invention is characterized in that the agent includes a compound of formula (I) in which X denotes oxygen and Y denotes sulfur and only one of the two residues R1 or R2 denotes hydrogen.

A further preferred embodiment of the first subject matter of the invention is characterized in that the agent includes a compound of formula (I) in which X and Y do not simultaneously denote oxygen and one of the two residues R1 or R2 denotes hydrogen and the other residue R2 or R1 denotes a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

A further preferred embodiment of the first subject matter of the invention is characterized in that the agent includes a compound of formula (I) in which X denotes oxygen and Y denotes sulfur and one of the two residues R1 or R2 denotes hydrogen and the other residue R2 or R1 denotes a methoxy group.

A further preferred embodiment of the first subject matter of the invention is characterized in that the agent includes a compound of formula (I) in which X denotes oxygen and Y denotes sulfur and the two residues R1 and R2 mutually independently denote a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

A further preferred embodiment of the first subject matter of the invention is characterized in that the agent includes a compound of formula (I) in which X denotes oxygen and Y denotes sulfur and the two residues R1 and R2 denote a methoxy group.

A further preferred embodiment of the first subject matter of the invention is characterized in that the agent includes a compound of formula (I) in which X denotes oxygen and Y denotes sulfur and exactly one of the residues R3, R4, R5 or R6 denotes a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group and the other three residues are hydrogen atoms.

A further preferred embodiment of the first subject matter of the invention is characterized in that the agent includes a compound of formula (I) in which X denotes oxygen and Y denotes sulfur and exactly one of the residues R3, R4, R5 or R6 denotes a methyl group and the other three residues are hydrogen atoms.

A further preferred embodiment of the first subject matter of the invention is characterized in that the agent includes a compound of formula (I) in which X and Y denote a group N—H and only one of the two residues R1 or R2 denotes hydrogen.

A further preferred embodiment of the first subject matter of the invention is characterized in that the agent includes a compound of formula (I) in which X and Y do not denote a group N—H and one of the two residues R1 or R2 denotes hydrogen and the other residue R2 or R1 denotes a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

A further preferred embodiment of the first subject matter of the invention is characterized in that the agent includes a compound of formula (I) in which X and Y denote a group N—H and one of the two residues R1 or R2 denotes hydrogen and the other residue R2 or R1 denotes a methoxy group.

A further preferred embodiment of the first subject matter of the invention is characterized in that the agent includes a compound of formula (I) in which X and Y denote a group N—H and the two residues R1 and R2 mutually independently denote a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

A further preferred embodiment of the first subject matter of the invention is characterized in that the agent includes a compound of formula (I) in which X and Y denote a group N—H and the two residues R1 and R2 denote a methoxy group.

A further preferred embodiment of the first subject matter of the invention is characterized in that the agent includes a compound of formula (I) in which X and Y denote a group N—H and exactly one of the residues R3, R4, R5 or R6 denotes a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group and the other three residues are hydrogen atoms.

A further preferred embodiment of the first subject matter of the invention is characterized in that the agent includes a compound of formula (I) in which X and Y denote a group N—H and exactly one of the residues R3, R4, R5 or R6 denotes a methyl group and the other three residues are hydrogen atoms.

A further embodiment of the first subject matter of the invention is characterized in that the agent includes at least one compound according to formula (I) which is selected from

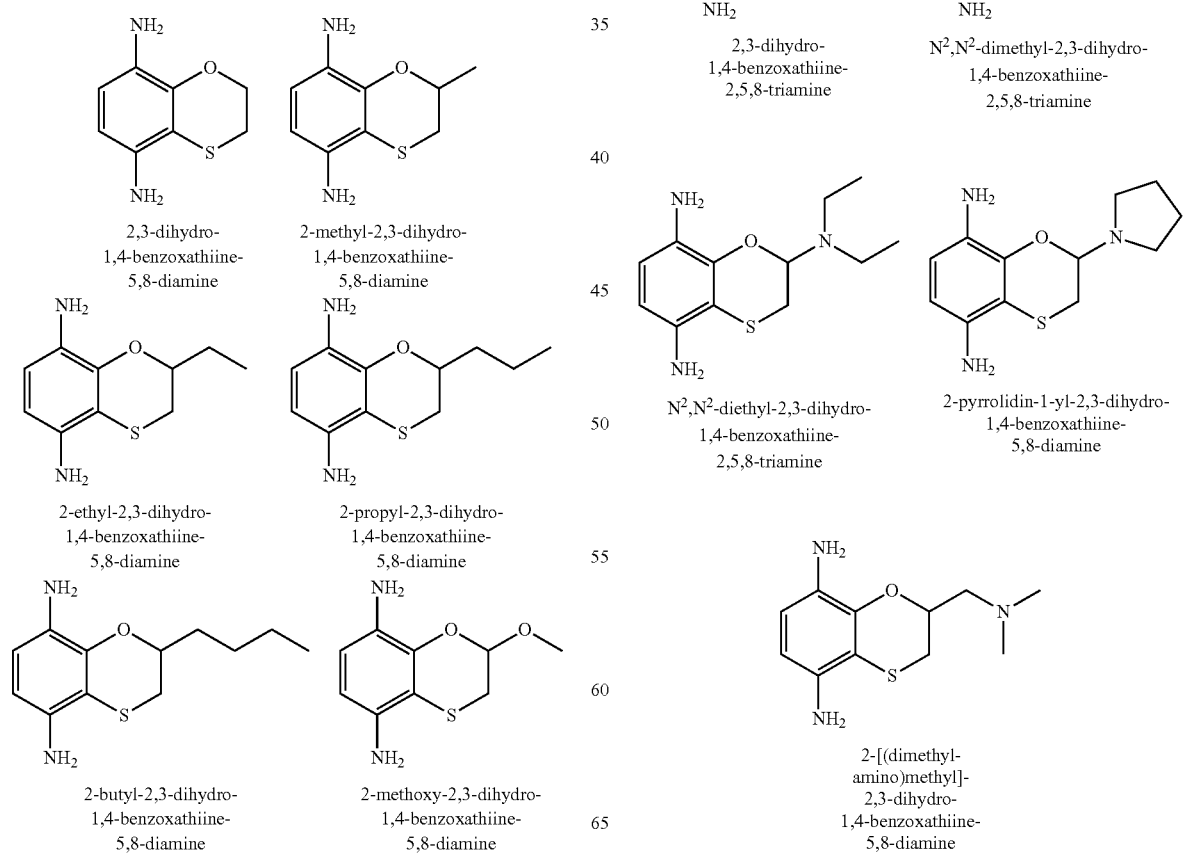

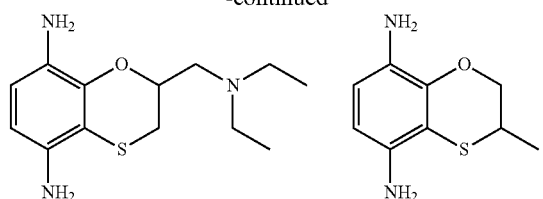

2-[(diethylamino)methyl]-
2,3-dihydro-
1,4-benzoxathiine-
5,8-diamine 3-methyl-
2,3-dihydro-
1,4-benzoxathiine-
5,8-diamine

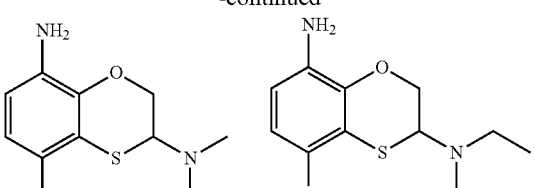

N³,N³-dimethyl-
2,3-dihydro-
1,4-benzoxathiine-
3,5,8-triamine

N³,N³-diethyl-2,3-dihydro-
1,4-benzoxathiine-
2,5,8-triamine

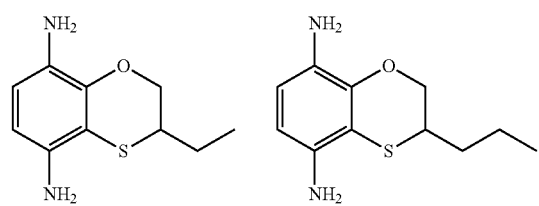

3-ethyl-
2,3-dihydro-
1,4-benzoxathiine-
5,8-diamine 3-propyl-
2,3-dihydro-
1,4-benzoxathiine-
5,8-diamine

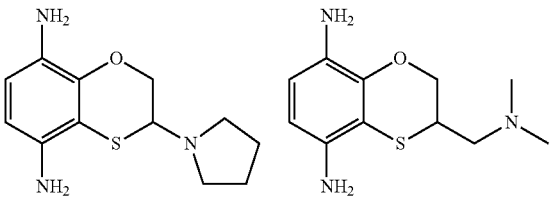

3-pyrrolidin-1-yl-
2,3-dihydro-
1,4-benzoxathiine-
5,8-diamine

3[(dimethyl-
amino)methyl]-
2,3-dihydro-
1,4-benzoxathiine-
5,8-diamine

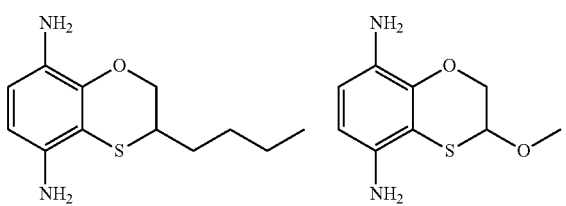

3-butyl-
2,3-dihydro-
1,4-benzoxathiine-
5,8-diamine 3-methoxy-
2,3-dihydro-
1,4-benzoxathiine-
5,8-diamine

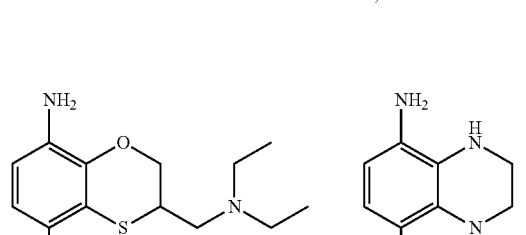

3-[(diethylamino)methyl]-
2,3-dihydro-1,4-benzoxathiine-
5,8-diamine 1,2,3,4-
tetrahydroquinoxaline-
5,8-diamine

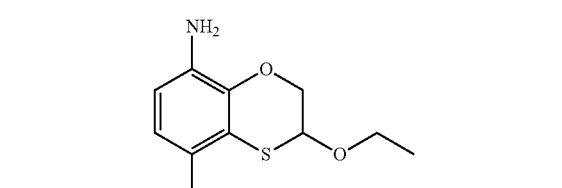

3-ethoxy-
2,3-dihydro-
1,4-benzoxathiine-
5,8-diamine

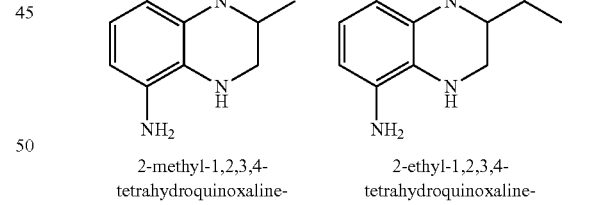

2-methyl-1,2,3,4-
tetrahydroquinoxaline-
5,8-diamine 2-ethyl-1,2,3,4-
tetrahydroquinoxaline-
5,8-diamine

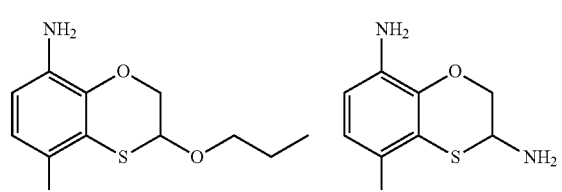

3-propoxy-
2,3-dihydro-
1,4-benzoxathiine-
5,8-diamine 2,3-dihydro-
1,4-benzoxathiine-
3,5,8-triamine

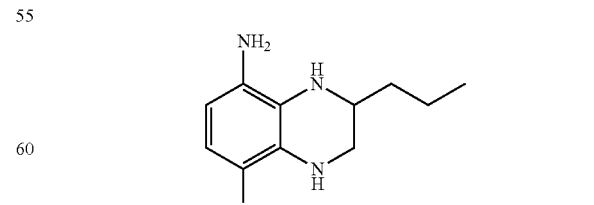

2-propyl-1,2,3,4-
tetrahydroquinoxaline-
5,8-diamine

-continued

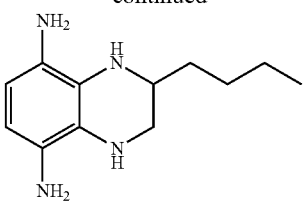

2-butyl-1,2,3,4-
tetrahydroquinoxaline-
5,8-diamine

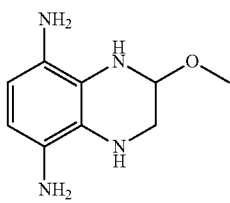 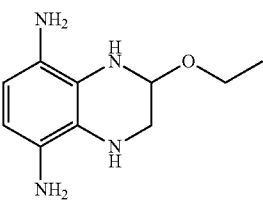

2-methoxy-1,2,3,4-
tetrahydroquinoxaline-
5,8-diamine 2-ethoxy-1,2,3,4-
tetrahydroquinoxaline-
5,8-diamine

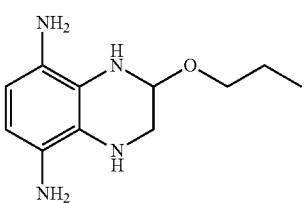

2-propoxy-1,2,3,4-
tetrahydroquinoxaline-
5,8-diamine

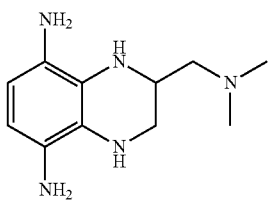

2-[(dimethyl-
amino)methyl]-
1,2,3,4-
tetrahydroquinoxaline-
5,8-diamine

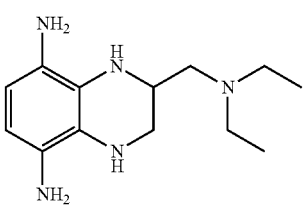

2-[(dimethylamino)methyl]-
1,2,3,4-
tetrahydroquinoxaline-
5,8-diamine

-continued

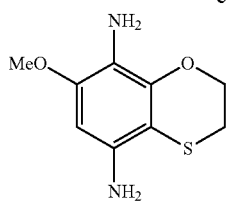 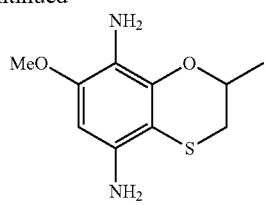

5-amino-7-methoxy-2,3-
dihydro-1,4-benzoxathiin-
8-ylamine 5-amino-7-methoxy-2-
methyl-2,3-dihydro-
1,4-benzoxathiin-8-ylamine

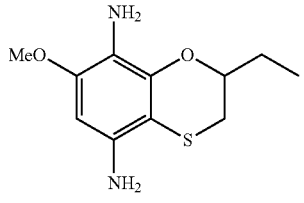

5-amino-7-methoxy-2-
ethyl-2,3-dihydro-
1,4-benzoxathiin-8-ylamine

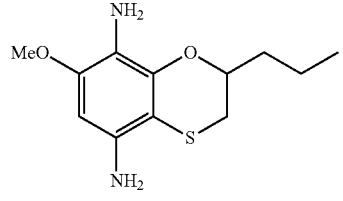

5-amino-7-methoxy-2-
propyl-2,3-dihydro-
1,4-benzoxathiin-8-ylamine

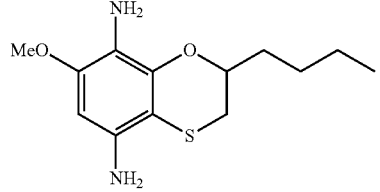

5-amino-7-methoxy-2-
butyl-2,3-dihydro-
1,4-benzoxathiin-8-ylamine

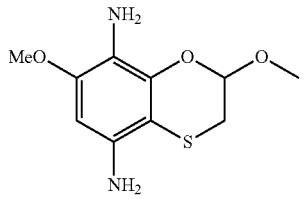

2,7-dimethoxy-2,3-dihydro-
1,4-benzoxathiine-5,8-diamine

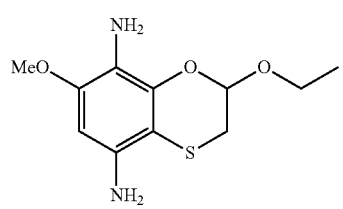

2-ethoxy-7-methoxy-2,3-dihydro-
1,4-benzoxathiine-5,8-diamine

-continued

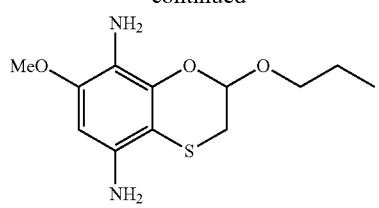

2-propoxy-7-methoxy-2,3-dihydro-
1,4-benzoxathiine-5,8-diamine

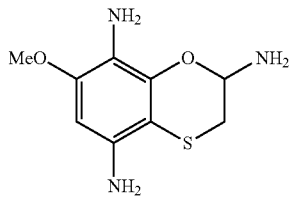

2,5-diamino-7-methoxy-2,3-dihydro-
1,4-benzoxathiin-8-ylamine

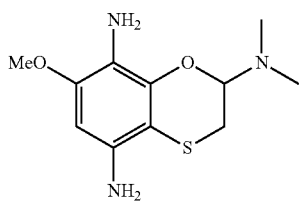

5-amino-2-(dimethylamino)-
7-methoxy-2,3-dihydro-
1,4-benzoxathiin-8-ylamine

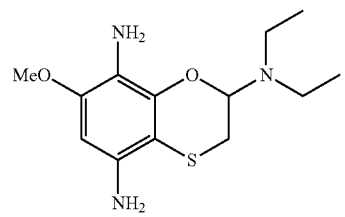

5-amino-2-(diethylamino)-
7-methoxy-2,3-dihydro-
1,4-benzoxathiin-8-ylamine

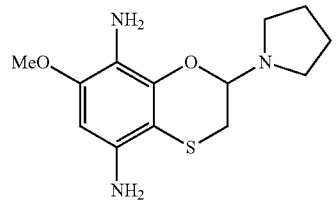

5-amino-7-methoxy-2-pyrrolidin-1-yl-
2,3-dihydro-
1,4-benzoxathiin-8-ylamine

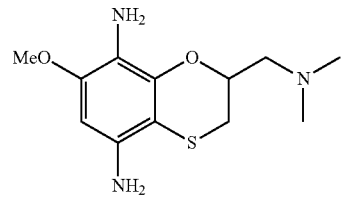

2-[(dimethyl-
amino)methyl]-7-methoxy-
2,3-dihydro-
1,4-benzoxathiine-5,8-diamine -continued

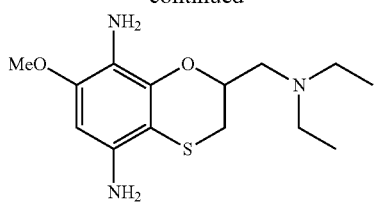

2-[(diethylamino)methyl]-7-methoxy-
2,3-dihydro-
1,4-benzoxathiine-5,8-diamine

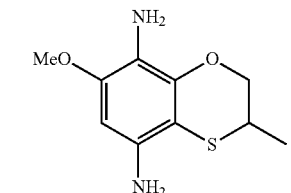   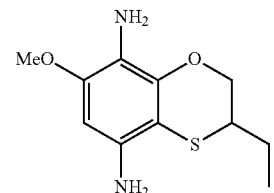

5-amino-7-methoxy-3-
methyl-2,3-dihydro-
1,4-benzoxathiin-8-ylamine 5-amino-7-methoxy-3-
ethyl-2,3-dihydro-
1,4-benzoxathiin-8-ylamine

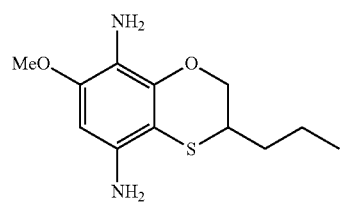

5-amino-7-methoxy-3-
propyl-2,3-dihydro-
1,4-benzoxathiin-8-ylamine

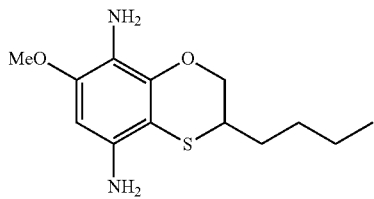

5-amino-7-methoxy-3-
butyl-2,3-dihydro-
1,4-benzoxathiin-8-ylamine

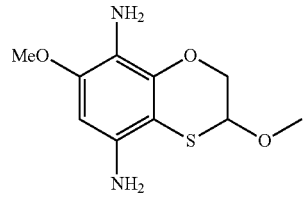

3,7-dimethoxy-2,3-dihydro-1,4-
benzoxathiine-5,8-diamine

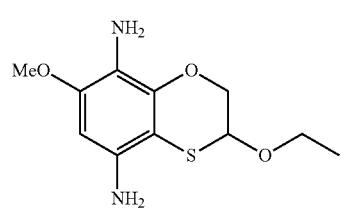

3-ethoxy-7-methoxy-2,3-dihydro-1,4-
benzoxathiine-5,8-diamine

-continued

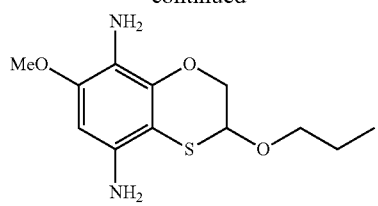

3-propoxy-7-methoxy-2,3-dihydro-1,4-
benzoxathiine-5,8-diamine

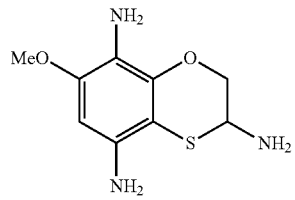

3,5-diamino-7-methoxy-
2,3-dihydro-1,4-
benzoxathiin-8-ylamine

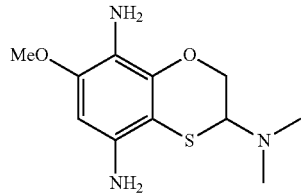

5-amino-3-(dimethylamino)-
7-methoxy-2,3-dihydro-1,4-
benzoxathiin-8-ylamine

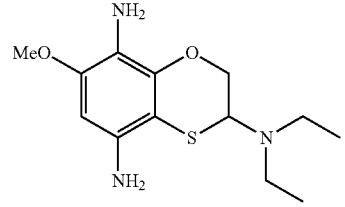

5-amino-3-(diethylamino)-
7-methoxy-2,3-dihydro-1,4-
benzoxathiin-8-ylamine

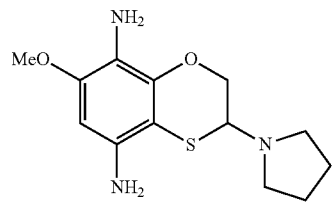

5-amino-7-methoxy-3-
pyrrolidin-1-yl-2,3-dihydro-1,4-
benzoxathiin-8-ylamine

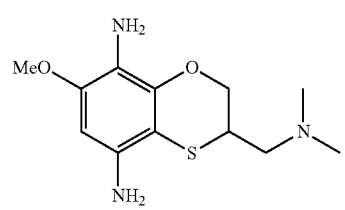

3-[(dimethyl-
amino)methyl]-7-methoxy-2,3-
dihydro-1,4-benzoxathiine-5,8-diamine -continued

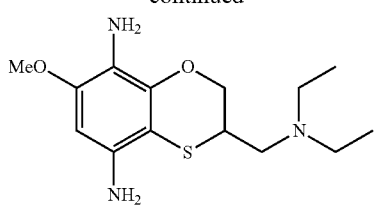

3-[(diethylamino)methyl]-7-
methoxy-2,3-dihydro-1,4-
benzoxathiine-5,8-diamine

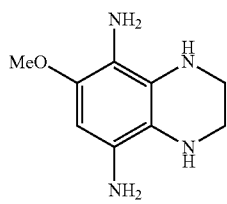   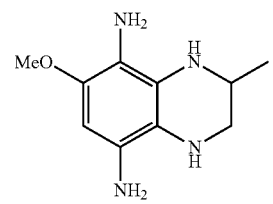

7-methoxy-1,2,3,4-
tetrahydroquinoxaline-
5,8-diamine 7-methoxy-2-methyl-
1,2,3,4-tetrahydroquinoxaline-
5,8-diamine

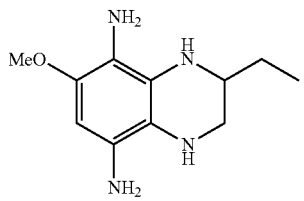

7-methoxy-2-ethyl-
1,2,3,4-tetrahydroquinoxaline-
5,8-diamine

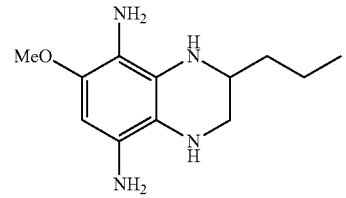

7-methoxy-2-propyl-
1,2,3,4-tetrahydroquinoxaline-
5,8-diamine

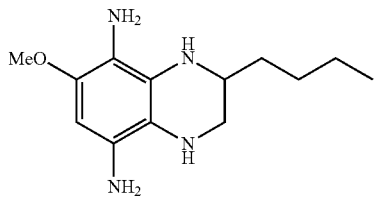

7-methoxy-2-butyl-
1,2,3,4-tetrahydroquinoxaline-
5,8-diamine

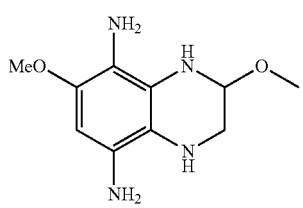

2,7-dimethoxy-
1,2,3,4-tetrahydroquinoxaline-
5,8-diamine

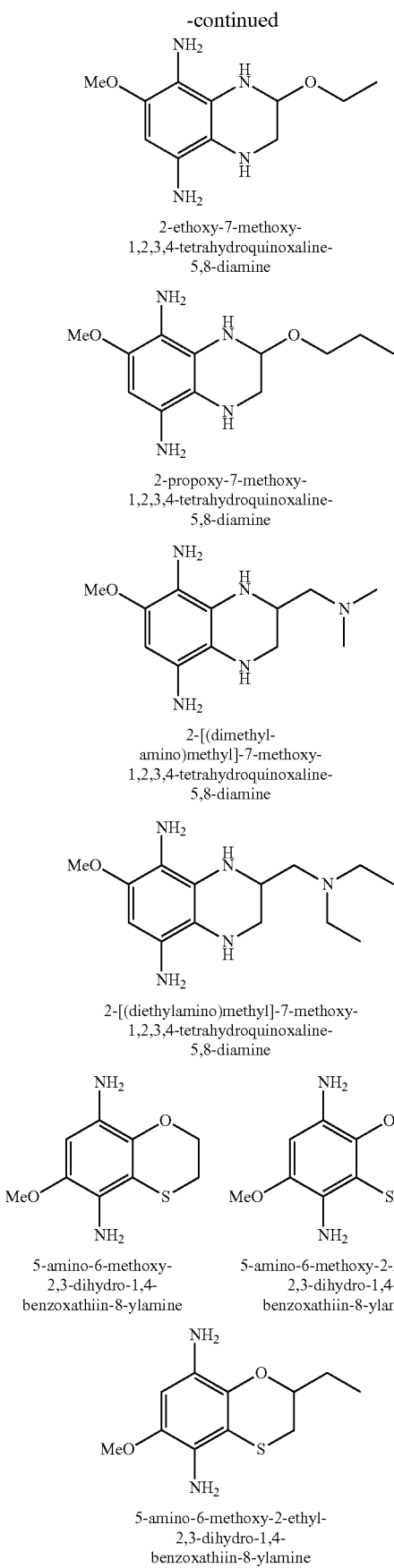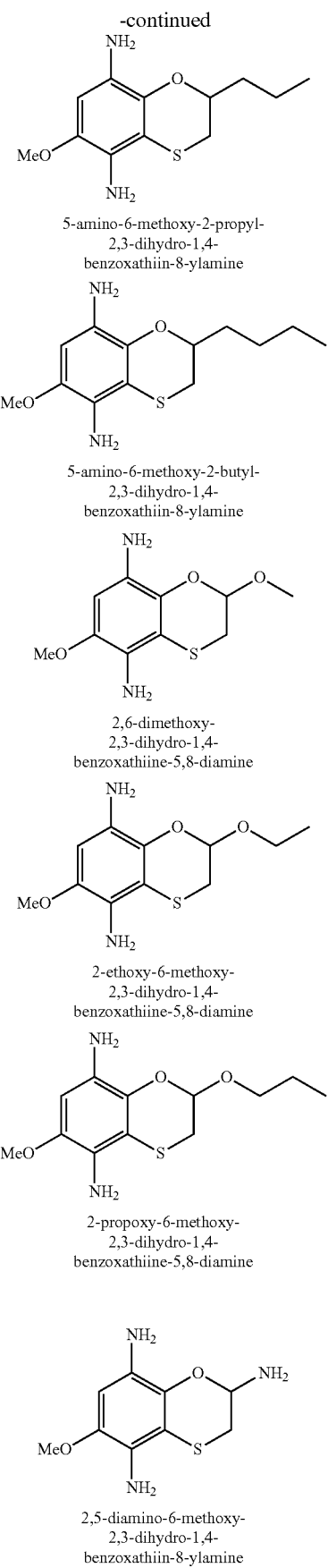

-continued

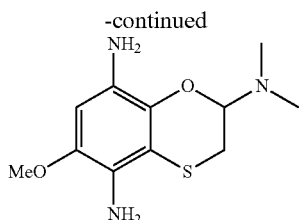

5-amino-2-(dimethylamino)-6-methoxy-
2,3-dihydro-1,4-
benzoxathiin-8-ylamine

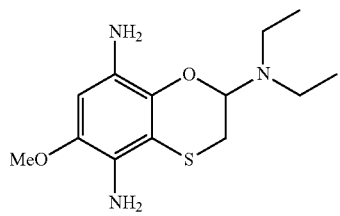

5-amino-2-(diethylamino)-6-methoxy-
2,3-dihydro-1,4-
benzoxathiin-8-ylamine

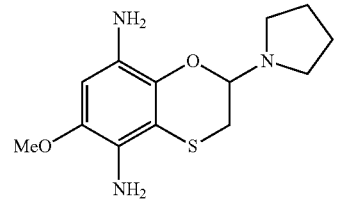

5-amino-6-methoxy-2-pyrrolidin-1-yl-
2,3-dihydro-1,4-
benzoxathiin-8-ylamine

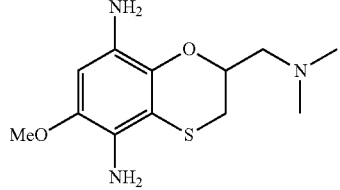

2-[(dimethyl-
amino)methyl]-6-methoxy-
2,3-dihydro-1,4-
benzoxathiine-5,8-diamine

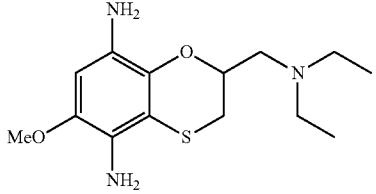

2-[(diethylamino)methyl]-6-methoxy-
2,3-dihydro-1,4-
benzoxathiine-5,8-diamine

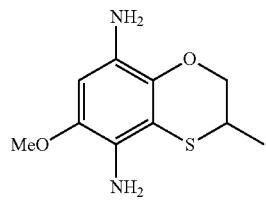

5-amino-6-methoxy-3-methyl-
2,3-dihydro-1,4-
benzoxathiin-8-ylamine

-continued

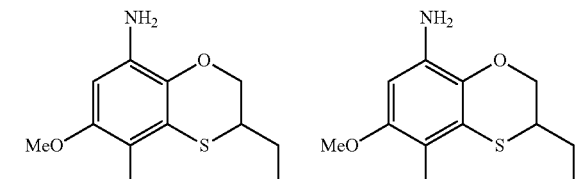

5-amino-6-methoxy-3-ethyl-
2,3-dihydro-1,4-
benzoxathiin-8-ylamine 5-amino-6-methoxy-3-propyl-
2,3-dihydro-1,4-
benzoxathiin-8-ylamine

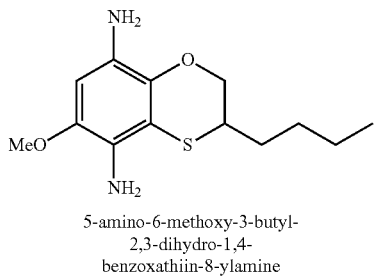

5-amino-6-methoxy-3-butyl-
2,3-dihydro-1,4-
benzoxathiin-8-ylamine

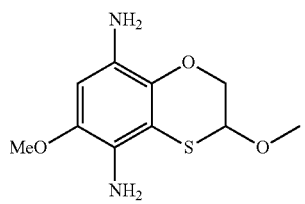

3,6-dimethoxy-
2,3-dihydro-1,4-
benzoxathiine-5,8-diamine

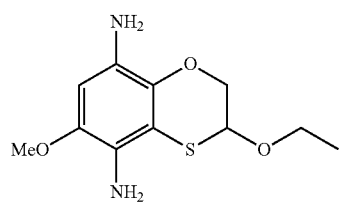

3-ethoxy-6-methoxy-
2,3-dihydro-1,4-
benzoxathiine-5,8-diamine

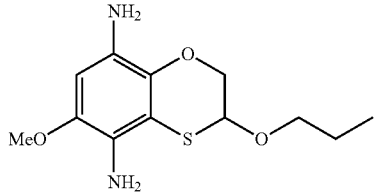

3-propoxy-6-methoxy-
2,3-dihydro-1,4-
benzoxathiine-5,8-diamine

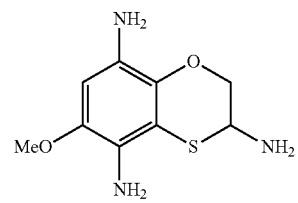

3,5-diamino-6-methoxy-
2,3-dihydro-1,4-
benzoxathiin-8-ylamine

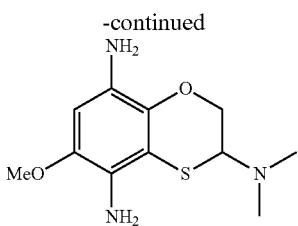

5-amino-3-(dimethylamino)-6-
methoxy-2,3-dihydro-1,4-
benzoxathiin-8-ylamine

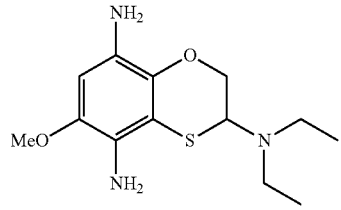

5-amino-3-(dimethylamino)-6-
methoxy-2,3-dihydro-1,4-
benzoxathiin-8-ylamine

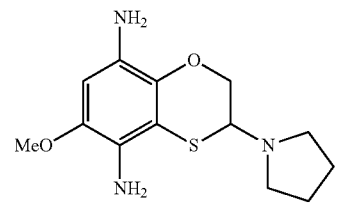

5-amino-6-methoxy-3-pyrrolidin-1-yl-
2,3-dihydro-1,4-
benzoxathiin-8-ylamine

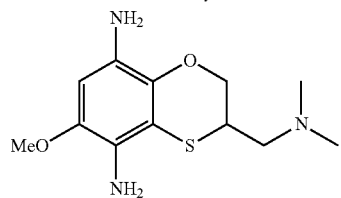

3-[(dimethyl-
amino)methyl]-6-methoxy-
2,3-dihydro-1,4-
benzoxathiine-5,8-diamine

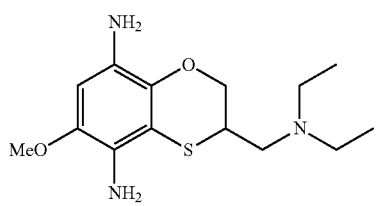

3-[(diethylamino)methyl]-6-methoxy-
2,3-dihydro-1,4-
benzoxathiine-5,8-diamine

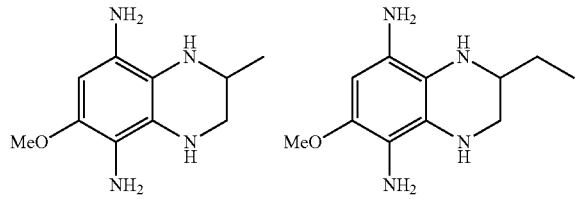

6-methoxy-2-methyl-1,2,3,4-
tetrahydroquinoxaline-
5,8-diamine 6-methoxy-2-ethyl-1,2,3,4-
tetrahydroquinoxaline-
5,8-diamine

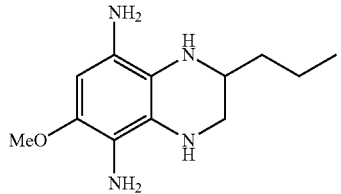

6-methoxy-2-propyl-1,2,3,4-
tetrahydroquinoxaline-
5,8-diamine

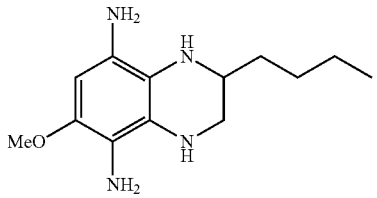

6-methoxy-2-butyl-1,2,3,4-
tetrahydroquinoxaline-
5,8-diamine

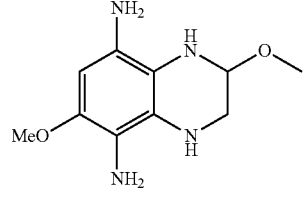

2,6-dimethoxy-1,2,3,4-
tetrahydroquinoxaline-
5,8-diamine

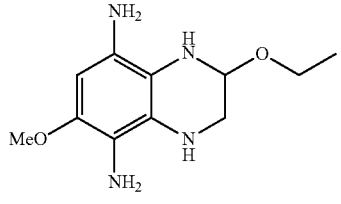

2-ethoxy-6-methoxy-1,2,3,4-
tetrahydroquinoxaline-
5,8-diamine

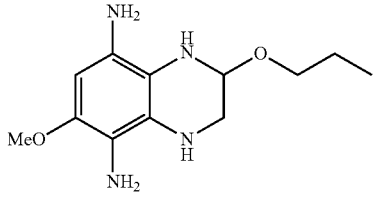

2-propoxy-6-methoxy-1,2,3,4-
tetrahydroquinoxaline-
5,8-diamine

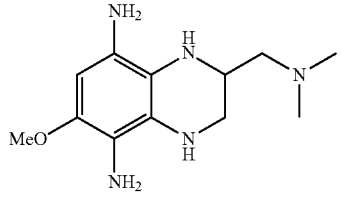

2-[(dimethyl-
amino)methyl]-6-methoxy-
1,2,3,4-
tetrahydroquinoxaline-
5,8-diamine

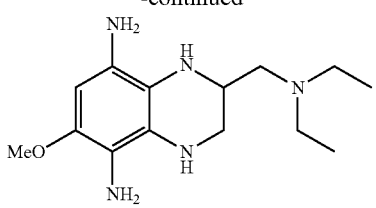

2-[(dimethylamino)methyl]-6-methoxy-
1,2,3,4-
tetrahydroquinoxaline-
5,8-diamine

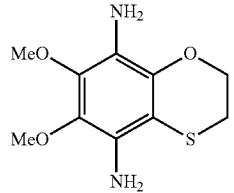

5-amino-6,7-dimethoxy-2,3-
dihydro-1,4-benzoxathiin-
8-ylamine

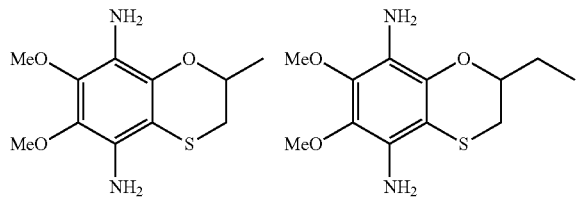

5-amino-6,7-dimethoxy-2-
methyl-2,3-dihydro-
1,4-benzoxathiin-8-ylamine 5-amino-6,7-dimethoxy-2-ethyl-2,3-
dihydro-1,4-benzoxathiin-
8-ylamine

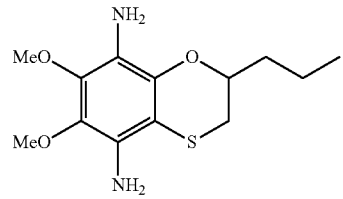

5-amino-6,7-dimethoxy-2-
propyl-2,3-dihydro-
1,4-benzoxathiin-8-ylamine

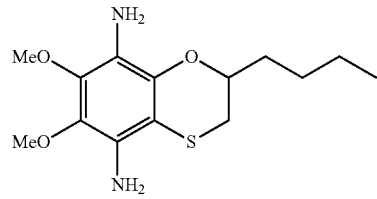

5-amino-6,7-dimethoxy-2-
butyl-2,3-dihydro-
1,4-benzoxathiin-8-ylamine

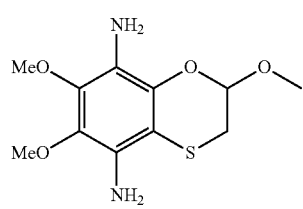

2,6,7-trimethoxy-2,3-dihydro-
1,4-benzoxathiine-5,8-diamine

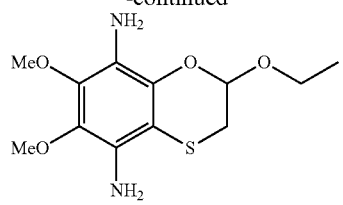

2-ethoxy-6,7-dimethoxy-2,3-dihydro-
1,4-benzoxathiine-5,8-diamine

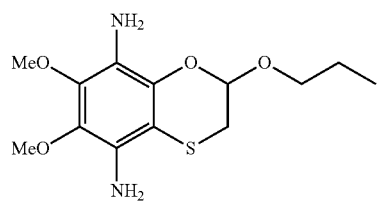

2-propoxy-6,7-dimethoxy-2,3-dihydro-
1,4-benzoxathiine-5,8-diamine

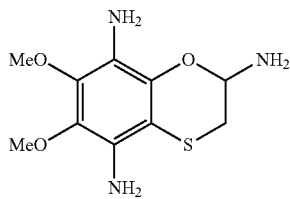

2,5-diamino-6,7-dimethoxy-2,3-dihydro-
1,4-benzoxathiin-8-ylamine

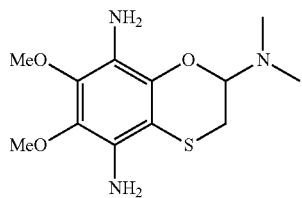

5-amino-2-(dimethylamino)-
6,7-dimethoxy-2,3-dihydro-
1,4-benzoxathiin-8-ylamine

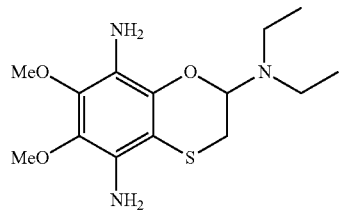

5-amino-2-(diethylamino)-
6,7-dimethoxy-2,3-dihydro-
1,4-benzoxathiin-8-ylamine

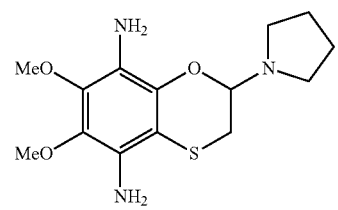

5-amino-6,7-dimethoxy-2-pyrrolidin-1-yl-
2,3-dihydro-
1,4-benzoxathiin-8-ylamine

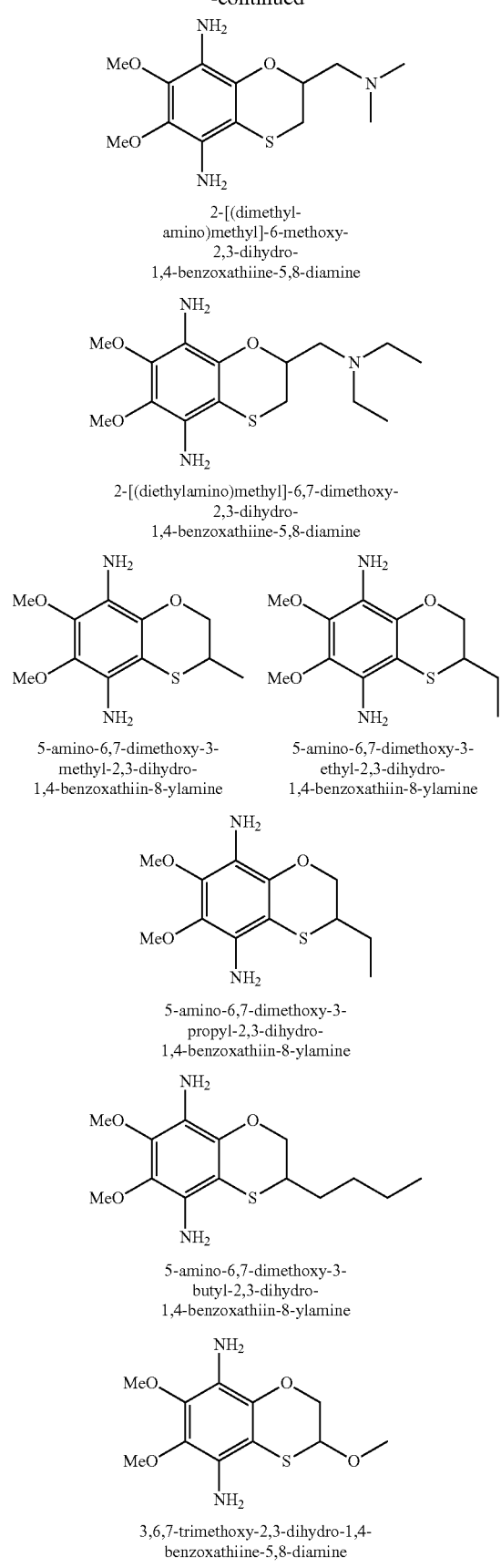
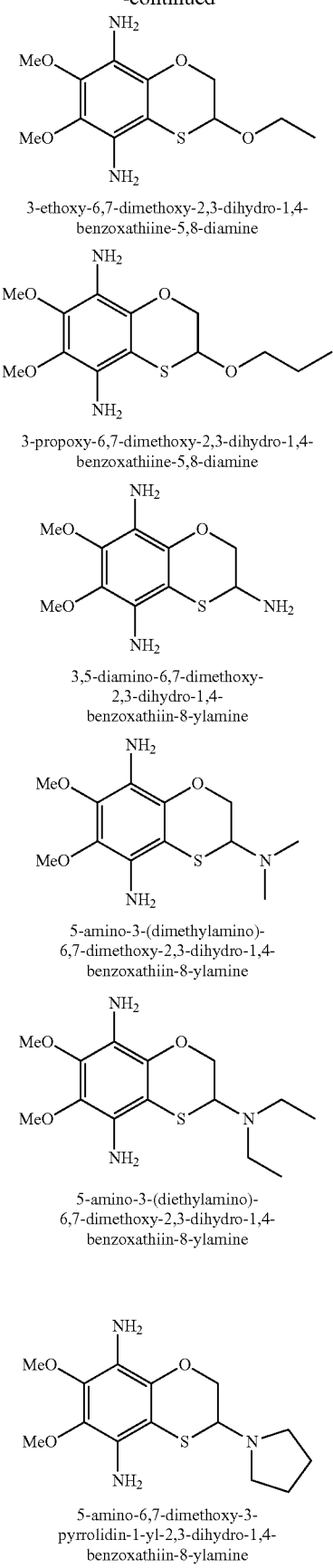

2-[(dimethyl-amino)methyl]-6-methoxy-2,3-dihydro-1,4-benzoxathiine-5,8-diamine

2-[(diethylamino)methyl]-6,7-dimethoxy-2,3-dihydro-1,4-benzoxathiine-5,8-diamine 5-amino-6,7-dimethoxy-3-methyl-2,3-dihydro-1,4-benzoxathiin-8-ylamine 5-amino-6,7-dimethoxy-3-ethyl-2,3-dihydro-1,4-benzoxathiin-8-ylamine 5-amino-6,7-dimethoxy-3-propyl-2,3-dihydro-1,4-benzoxathiin-8-ylamine 5-amino-6,7-dimethoxy-3-butyl-2,3-dihydro-1,4-benzoxathiin-8-ylamine 3,6,7-trimethoxy-2,3-dihydro-1,4-benzoxathiine-5,8-diamine 3-ethoxy-6,7-dimethoxy-2,3-dihydro-1,4-benzoxathiine-5,8-diamine 3-propoxy-6,7-dimethoxy-2,3-dihydro-1,4-benzoxathiine-5,8-diamine 3,5-diamino-6,7-dimethoxy-2,3-dihydro-1,4-benzoxathiin-8-ylamine 5-amino-3-(dimethylamino)-6,7-dimethoxy-2,3-dihydro-1,4-benzoxathiin-8-ylamine 5-amino-3-(diethylamino)-6,7-dimethoxy-2,3-dihydro-1,4-benzoxathiin-8-ylamine 5-amino-6,7-dimethoxy-3-pyrrolidin-1-yl-2,3-dihydro-1,4-benzoxathiin-8-ylamine

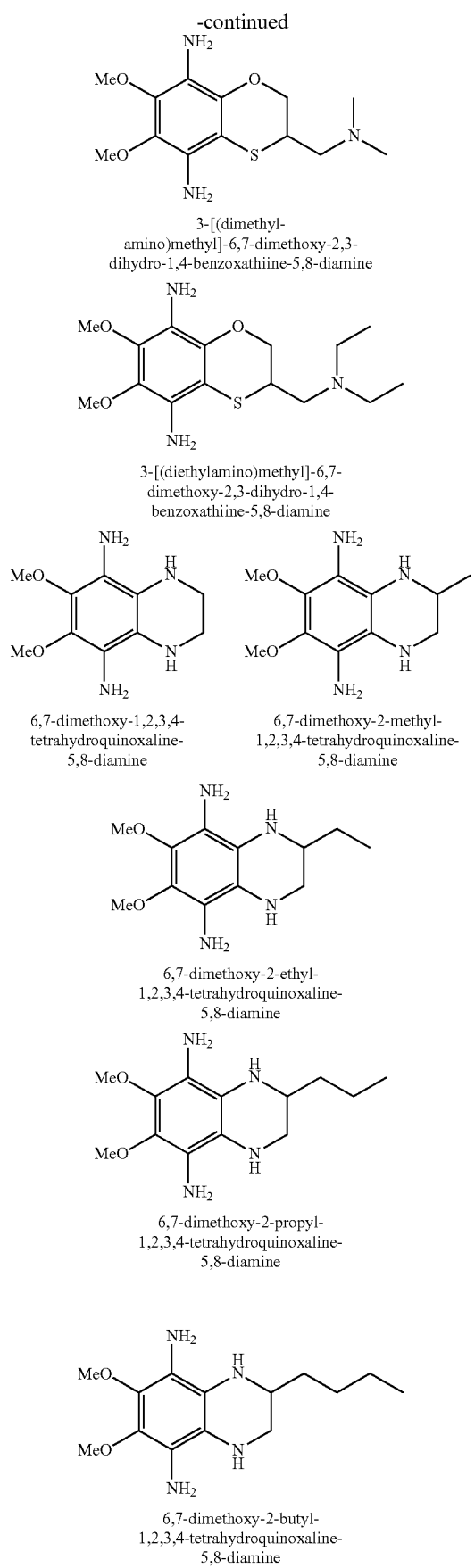
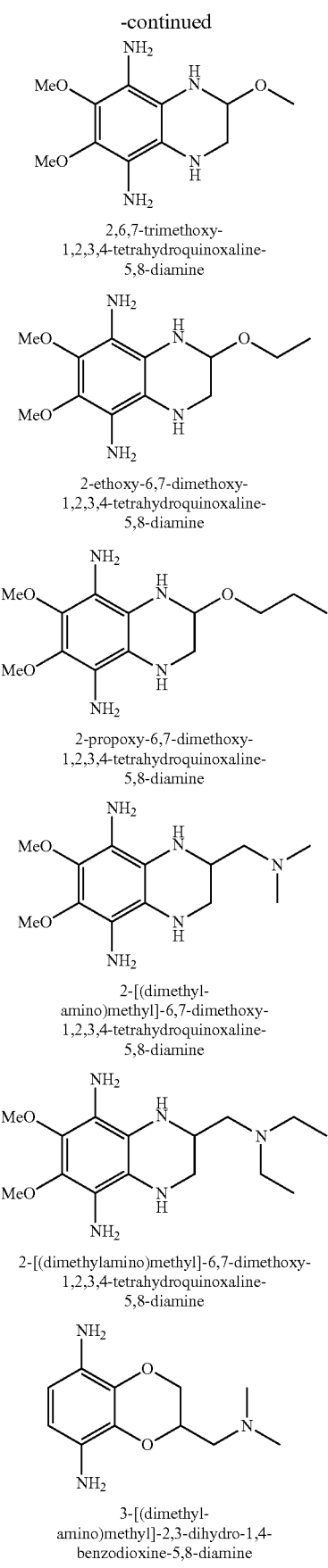

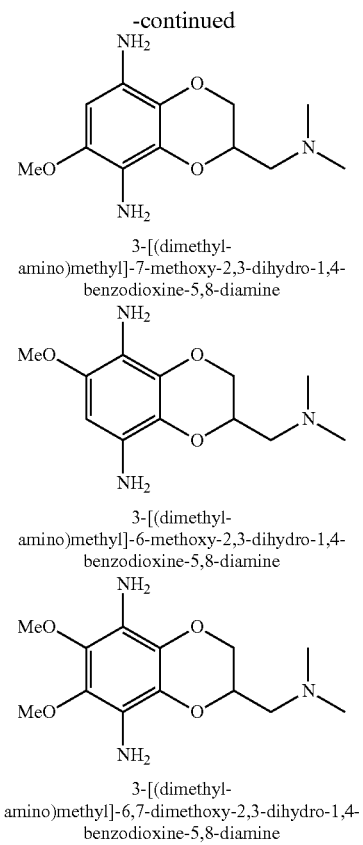

3-[(dimethyl-amino)methyl]-7-methoxy-2,3-dihydro-1,4-benzodioxine-5,8-diamine

3-[(dimethyl-amino)methyl]-6-methoxy-2,3-dihydro-1,4-benzodioxine-5,8-diamine

3-[(dimethyl-amino)methyl]-6,7-dimethoxy-2,3-dihydro-1,4-benzodioxine-5,8-diamine and/or the physiologically acceptable salts thereof.

Within the group of preferred compounds, the following compounds are of particular significance due the particularly advantageous applicational properties thereof: 2,3-dihydro-1,4-benzoxathiine-5,8-diamine, 2-methoxy-2,3-dihydro-1,4-benzoxathiine-5,8-diamine, 2-ethoxy-2,3-dihydro-1,4-benzoxathiine-5,8-diamine, $N^2,N^2$-dimethyl-2,3-dihydro-1,4-benzoxathiine-2,5,8-triamine, 2-[(dimethylamino)methyl]-2,3-dihydro-1,4-benzoxathiine-5,8-diamine, 3-methoxy-2,3-dihydro-1,4-benzoxathiine-5,8-diamine, $N^3,N^3$-dimethyl-2,3-dihydro-1,4-benzoxathiine-3,5,8-triamine, 3-[(dimethylamino)methyl]-2,3-dihydro-1,4-benzoxathiine-5,8-diamine, 1,2,3,4-tetrahydroquinoxaline-5,8-diamine, 2-methyl-1,2,3,4-tetrahydroquinoxaline-5,8-diamine, 2-methoxy-1,2,3,4-tetrahydro quinoxaline-5,8-diamine, 2-[(dimethylamino)methyl]-1,2,3,4-tetrahydroquinoxaline-5,8-diamine, 5-amino-7-methoxy-2,3-dihydro-1,4-benzoxathiin-8-ylamine, 2,7-dimethoxy-2,3-dihydro-1,4-benzoxathiine-5,8-diamine, 2-[(di-methylamino)methyl]-7-methoxy-2,3-dihydro-1,4-benzoxathiine-5,8-diamine, 3,7-dimethoxy-2,3-dihydro-1,4-benzoxathiine-5,8-diamine, 3-[(dimethylamino)methyl]-7-methoxy-2,3-dihydro-1,4-benzoxathiine-5,8-diamine, 7-methoxy-1,2,3,4-tetrahydro quinoxaline-5,8-diamine, 2,7-dimethoxy-1,2,3,4-tetrahydroquinoxaline-5,8-diamine, 2-[(dimethylamino)methyl]-7-methoxy-1,2,3,4-tetrahydroquinoxaline-5,8-diamine, 5-amino-6-methoxy-2-methyl-2,3-dihydro-1,4-benzoxathiin-8-ylamine, 5-amino-6-methoxy-2,3-dihydro-1,4-benzoxathiin-8-ylamine, 2,6-dimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6-dimethoxy-2,3-dihydro-1,4-benzoxathiine-5,8-diamine, 3-[(dimethylamino)methyl]-6-methoxy-2,3-dihydro-1,4-benzoxathiine-5,8-diamine, 2,6-dimethoxy-1,2,3,4-tetrahydroquinoxaline-5,8-diamine, 2-[(dimethylamino)methyl]-6-methoxy-1,2,3,4-tetrahydroquinoxaline-5,8-diamine, 5-amino-6,7-dimethoxy-2,3-dihydro-1,4-benzoxathiin-8-ylamine, 2,6,7-trimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6,7-trimethoxy-2,3-dihydro-1,4-benzoxathiine-5,8-diamine, 3-[(dimethylamino)methyl]-6,7-dimethoxy-2,3-dihydro-1,4-benzoxathiine-5,8-diamine, 6,7-dimethoxy-1,2,3,4-tetrahydro quinoxaline-5,8-diamine, 2,6,7-trimethoxy-1,2,3,4-tetrahydro quinoxaline-5,8-diamine, 2-[(dimethylamino)methyl]-6,7-dimethoxy-1,2,3,4-tetrahydroquinoxaline-5,8-diamine, 6,7-dimethoxy-(2-dimethylaminomethyl)-2,3-dihydro-1,4-benzodioxine-5,8-diamine, (2-dimethylamino)-2,3-dihydro-1,4-benzodioxine-5,8-diamine, and the physiologically acceptable salts thereof.

A further embodiment of the first subject matter of the invention is characterized in that the agent includes at least one compound according to formula (I) which is selected from 2,3-dihydro-1,4-benzoxathiine-5,8-diamine, 2-methoxy-2,3-dihydro-1,4-benzoxathiine-5,8-diamine, 2-ethoxy-2,3-dihydro-1,4-benzoxathiine-5,8-diamine, $N^2,N^2$-dimethyl-2,3-dihydro-1,4-benzoxathiine-2,5,8-triamine, 2-[(dimethylamino)methyl]-2,3-dihydro-1,4-benzoxathiine-5,8-diamine, 3-methoxy-2,3-dihydro-1,4-benzoxathiine-5,8-diamine, $N^3,N^3$-dimethyl-2,3-dihydro-1,4-benzoxathiine-3,5,8-triamine, 3-[(dimethylamino)methyl]-2,3-dihydro-1,4-benzoxathiine-5,8-diamine, 1,2,3,4-tetrahydroquinoxaline-5,8-diamine, 2-methyl-1,2,3,4-tetrahydroquinoxaline-5,8-diamine, 2-methoxy-1,2,3,4-tetrahydroquinoxaline-5,8-diamine, 2-[(dimethylamino)methyl]-1,2,3,4-tetrahydro quinoxaline-5,8-diamine, 5-amino-7-methoxy-2,3-dihydro-1,4-benzoxathiin-8-ylamine, 2,7-dimethoxy-2,3-dihydro-1,4-benzoxathiine-5,8-diamine, 2-[(dimethylamino)methyl]-7-methoxy-2,3-dihydro-1,4-benzoxathiine-5,8-diamine, 3,7-dimethoxy-2,3-dihydro-1,4-benzoxathiine-5,8-diamine, 3-[(dimethylamino)methyl]-7-methoxy-2,3-dihydro-1,4-benzoxathiine-5,8-diamine, 7-methoxy-1,2,3,4-tetrahydroquinoxaline-5,8-diamine, 2,7-dimethoxy-1,2,3,4-tetrahydroquinoxaline-5,8-diamine, 2-[(dimethylamino)methyl]-7-methoxy-1,2,3,4-tetrahydro quinoxaline-5,8-diamine, 5-amino-6-methoxy-2-methyl-2,3-dihydro-1,4-benzoxathiin-8-ylamine, 5-amino-6-methoxy-2,3-dihydro-1,4-benzoxathiin-8-ylamine, 2,6-dimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6-dimethoxy-2,3-dihydro-1,4-benzoxathiine-5,8-diamine, 3-[(dimethylamino)methyl]-6-methoxy-2,3-dihydro-1,4-benzoxathiine-5,8-diamine, 2,6-dimethoxy-1,2,3,4-tetrahydroquinoxaline-5,8-diamine, 2-[(dimethylamino)methyl]-6-methoxy-1,2,3,4-tetrahydro quinoxaline-5,8-diamine, 5-amino-6,7-dimethoxy-2,3-dihydro-1,4-benzoxathiin-8-ylamine, 2,6,7-trimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6,7-trimethoxy-2,3-dihydro-1,4-benzoxathiine-5,8-diamine, 3-[(dimethylamino)methyl]-6,7-dimethoxy-2,3-dihydro-1,4-benzoxathiine-5,8-diamine, 6,7-dimethoxy-1,2,3,4-tetrahydro quinoxaline-5,8-diamine, 2,6,7-trimethoxy-1,2,3,4-tetrahydro quinoxaline-5,8-diamine, 2-[(dimethylamino)methyl]-6,7-dimethoxy-1,2,3,4-tetrahydroquinoxaline-5,8-diamine, 6,7-dimethoxy-(2-dimethylaminomethyl)-2,3-dihydro-1,4-benzo dioxine-5,8-diamine, (2-dimethylamino)-2,3-dihydro-1,4-benzodioxine-5,8-diamine and the physiologically acceptable salts thereof.

The compounds according to the invention of formula (I) may include at least one carbon atom with four different substituents. Due to these stereogenic centers, stereoisomerism is possible in the group of substances. Enantiomerism or diastereoisomerism is possible in the compounds according to the invention. The current invention includes all the enantiomers and diastereomers of the invention, i.e. both the R enantiomer and the S enantiomer and, where 2 chiral centers are present, the S,S, R,R, S,R and R,S stereoisomers of each substance are according to the invention. It is furthermore possible both to use an equimolar mixture of the stereoisomers (in the case of an enantiomeric racemate) as an agent for coloring hair and to use any other conceivable molar ratio of the stereoisomers.

The compounds of formula (I) may be used in the form of the physiologically acceptable salts thereof, in particular the chlorides, sulfates and bromides. Further preferred salts are derived from sulfonic acids, such as benzenesulfonates, p-toluenesulfonates, $C_1$-$C_4$ alkanesulfonates, $C_1$-$C_4$ alkylsulfates or trifluoromethanesulfonates. Depending on the number of amino groups present in the compounds according to the invention, mono, di, tri, tetra and higher adducts may be present as salts.

Agents which are preferred according to the invention are characterized in that they include the compound according to formula (I) and/or the physiologically acceptable salts thereof in a proportion by weight of 0.001 to 10.0 wt. %, in particular 0.05 to 5 wt. %, relative to total weight of the ready-to-use agent.

The compounds of formula (I) may be present as the sole color-modifying compounds in the agent according to the invention. It is, however, preferred according to the invention for the agent additionally to include at least one oxidation dye precursor of the coupler component type.

In the context of oxidative coloring, coupler components alone do not form any significant coloring, but instead always require the presence of developer components.

Coupler components for the purposes of the invention permit at least one substitution of a chemical residue of the coupler by the oxidized form of the developer component. This results in the formation of covalent bonds between the coupler and developer component.

Coupler components according to the invention are preferably selected as at least one compound from one of the following classes:
  m-aminophenol and/or the derivatives thereof,
  m-diaminobenzene and/or the derivatives thereof,
  o-diaminobenzene and/or the derivatives thereof,
  o-aminophenol derivatives, such as for example o-aminophenol,
  naphthalene derivatives with at least one hydroxyl group,
  di- or trihydroxybenzene and/or the derivatives thereof,
  pyridine derivatives,
  pyrimidine derivatives,
  monohydroxyindole derivatives and/or monoaminoindole derivatives,
  monohydroxyindoline derivatives and/or monoaminoindoline derivatives,
  pyrazolone derivatives, such as for example 1-phenyl-3-methylpyrazol-5-one,
  morpholine derivatives, such as for example 6-hydroxybenzomorpholine or 6-aminobenzomorpholine,
  quinoxaline derivatives, such as for example 6-methyl-1,2,3,4-tetrahydroquinoxaline.

Mixtures of two or more compounds from one or more of these classes are also according to the invention for the purposes of this embodiment.

Coupler components which are more preferred according to the invention are selected from 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline or mixtures of these compounds or the physiologically acceptable salts of the above-stated compounds. Particularly preferred are resorcinol, 2-methylresorcinol, 5-amino-2-methylphenol, 3-aminophenol, 2-(2,4-diaminophenoxy)ethanol, 1,3-bis-(2,4-diaminophenoxy)propane, 1-methoxy-2-amino-4-(2'-hydroxyethylamino)benzene, 2-amino-3-hydroxypyridine and 1-naphthol and one of the physiologically acceptable salts thereof.

The coupler components are preferably used in a quantity of 0.0001 to 10 wt. %, preferably 0.01 to 5.0 wt. %, in each case relative to the ready-to-use agent.

In order to achieve balanced and subtle shades, it is advantageous according to the invention for the agent according to the invention to include further color-imparting components.

It may therefore be preferred according to the invention for the agent to include at least one further color-imparting component which is selected from additional oxidation dye precursors of the developer type and/or substantive dyes.

In addition to the oxidation dye precursors of the developer type according to formula (I), the agents according to the invention may additionally include at least one further developer component.

Preferred further developer components are selected from at least one compound from the group which is formed from p-phenylenediamine, p-tolylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, 2-methoxymethyl-p-phenylenediamine, N-(4-amino-3-methylphenyl)-N-[3-(1H-imidazol-1-yl)propyl]amine, N,N'-bis-(2-hydroxyethyl)-N,N'-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4'-aminophenyl)-1,4-diazacycloheptane, 1,10-bis-(2,5-diaminophenyl)-1,4,7,10-tetraoxadecane, 4-aminophenol, 4-amino-3-methylphenol, 4-amino-2-aminomethylphenol, 4-amino-2-(1,2-dihydroxyethyl)phenol and 4-amino-2-(diethylaminomethyl)phenol, 4,5-diamino-1-(2-hydroxyethyl)pyrazole, 2,4,5,6-tetraminopyrimidine, 4-hydroxy-2,5,6-triaminopyrimidine, 2-hydroxy-4,5,6-triaminopyrimidine, and the physiologically acceptable salts of these compounds. More preferred additional developer components are here p-tolylenediamine, 2-(2-hydroxyethyl)-p-phenylenediamine, 2-methoxymethyl-p-phenylenediamine, N-(4-amino-3-methylphenyl)-N-[3-(1H-imidazol-1-yl)propyl]amine, and/or 4,5-diamino-1-(2-hydroxyethyl)pyrazole and the physiologically acceptable salts thereof.

The additional developer components are preferably used in a quantity of 0.0001 to 10 wt. %, preferably 0.001 to 5 wt. %, in each case relative to the ready-to-use agent.

The agents according to the invention may furthermore include at least one substantive dye. These are dyes which key directly to the hair and do not need an oxidative process to develop the color. Substantive dyes are conventionally nitrophenylenediamines, nitroaminophenols, azo dyes, anthraquinones or indophenols.

The substantive dyes are in each case preferably used in a quantity of 0.001 to 20 wt. %, in particular of 0.05 to 5 wt. %, in each case relative to the total preparation for use. The total quantity of substantive dyes preferably amounts to at most 3 wt. %.

Substantive dyes may be subdivided into anionic, cationic and nonionic substantive dyes which are selected by a person skilled in the art in line with the requirements of the carrier base.

Preferred anionic substantive dyes are the compounds known by the international names or trade names bromophenol blue, tetrabromophenol blue, Acid Yellow 1, Yellow 10, Acid Yellow 23, Acid Yellow 36, Acid Orange 7, Acid Red 33, Acid Red 52, Pigment Red 57:1, Acid Blue 7, Acid Green 50, Acid Violet 43, Acid Black 1 and Acid Black 52.

Preferred cationic substantive dyes are Basic Blue 7, Basic Blue 26, Basic Violet 2 and Basic Violet 14, Basic Yellow 57, Basic Red 76, Basic Blue 16, Basic Blue 347 (Cationic Blue 347/Dystar), Basic Blue 99, Basic Brown 16 and Basic Brown 17 and Yellow 87, Basic Orange 31 and Basic Red 51.

Suitable nonionic substantive dyes are in particular nonionic nitro and quinone dyes and neutral azo dyes. Preferred nonionic substantive dyes are the compounds known by the international names or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9, and 1,4-diamino-2-nitrobenzene, 2-amino-4-nitrophenol, 1,4-bis-(2-hydroxyethyl)amino-2-nitrobenzene, 3-nitro-4-(2-hydroxyethyl) aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenol)amino]-benzoic acid, 6-nitro-1,2,3,4-tetrahydroquinoxaline, 2-hydroxy-1,4-naphthoquinone, picramic acid and the salts thereof, 2-amino-6-chloro-4-nitrophenol, 4-ethylamino-3-nitrobenzoic acid and 2-chloro-6-ethylamino-4-nitrophenol.

In addition to the compound according to formula (I), the agents according to the invention may also include nature-analogous dyes. Compositions according to the invention which include precursors of nature-analogous dyes are preferably used as coloring agents which function by atmospheric oxidation. In this embodiment, said compositions are consequently not combined with an additional oxidizing agent.

The dyes precursors are used in each case preferably in a quantity of 0.001 to 5 wt. %, relative to the entire preparation for use. Derivatives of 5,6-dihydroxyindoline are particularly suitable as precursors of nature-analogous hair dyes, in particular 5,6-dihydroxyindoline, N-methyl-5,6-dihydroxyindoline, N-ethyl-5,6-dihydroxyindoline, N-propyl-5,6-dihydroxyindoline, N-butyl-5,6-dihydroxyindoline and 5,6-dihydroxyindoline-2-carboxylic acid, and furthermore derivatives of 5,6-dihydroxyindole, in particular 5,6-dihydroxyindole, N-methyl-5,6-dihydroxyindole, N-ethyl-5,6-dihydroxyindole, N-propyl-5,6-dihydroxyindole, N-butyl-5,6-dihydroxyindole, 5,6-dihydroxyindole-2-carboxylic acid, and physiologically acceptable salts of the above-stated compounds.

In the case of oxidative colorings, the color may in principle be developed with atmospheric oxygen. Preferably, however, a chemical oxidizing agent is used, particularly when the intention is to lighten human hair as well as color it. This lightening effect may be desired independently of the dyeing method. Oxidizing agents which may be considered are persulfates, peroxodisulfates, chlorites, hypochlorites and in particular hydrogen peroxide and/or one of the solid addition products thereof onto organic or inorganic compounds.

In order to prevent the oxidizing agent from reacting prematurely and in an unwanted manner with the oxidation dye precursors, the oxidation dye precursors and oxidizing agent itself are expediently packaged separately from one another and only brought into contact immediately before use.

In a further embodiment of the present invention, preferred agents are therefore those which are characterized in that they are produced immediately before use by mixing at least two preparations, wherein the at least two preparations are provided in at least two separately packaged containers and wherein one container includes a coloring agent (A) which includes at least one oxidation dye precursor according to formula (I) in a cosmetic carrier, and a further container includes an oxidizing agent preparation (B) including at least one oxidizing agent.

The oxidizing agent preparation (B) preferably includes as oxidizing agent hydrogen peroxide and/or one of the solid addition products thereof onto organic or inorganic compounds, such as urea, melamine and sodium borate.

The quantity of oxidizing agent in the ready-to-use agent preferably amounts to 0.5 to 12 wt. %, preferably 2 to 10 wt. % more preferably to 3 to 6 wt. % (calculated as 100% $H_2O_2$), in each case relative to the ready-to-use agent.

According to the invention, however, the oxidation coloring agent may also be applied onto the hair together with a catalyst which activates the oxidation of the dye precursors. Such catalysts are for example specific enzymes, iodides, quinones or metal ions.

The agents are preferably provided as a liquid preparation and a surface-active substance is therefore additionally added to the agents, wherein such surface-active substances, are described depending on the area of application as surfactants or as emulsifiers: they are preferably selected from anionic, cationic, zwitterionic, amphoteric and nonionic surfactants and emulsifiers.

Agents which are preferred according to the invention are characterized in that the agent additionally includes at least one anionic surfactant. Preferred anionic surfactants are fatty acids, alkyl sulfates, alkyl ether sulfates and ether carboxylic acids with 10 to 20 C atoms in the alkyl group and up to 16 glycol ether groups per molecule. The anionic surfactants are used in proportions of 0.1 to 45 wt. %, preferably of 1 to 30 wt. % and particularly preferably of 1 to 15 wt. %, relative to the total quantity of the ready-to-use agent.

Agents which are preferred according to the invention are characterized in that the agent additionally includes at least one zwitterionic surfactant. Preferred zwitterionic surfactants are betaines, N-alkyl-N,N-dimethylammonium glycinates, N-acylaminopropyl-N,N-dimethylammonium glycinates, and 2-alkyl-3-carboxymethyl-3-hydroxyethylimidazolines. One preferred zwitterionic surfactant is known by the INCI name Cocamidopropyl Betaine.

Agents which are preferred according to the invention are characterized in that the agent additionally includes at least one amphoteric surfactant. Preferred amphoteric surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids. More preferred amphoteric surfactants are N-cocoalkyl aminopropionate, cocoacylaminoethyl aminopropionate and $C_{12}$-$C_{1s}$ acylsarcosine.

It has furthermore proven advantageous for the agents to include further non-ionogenic interfacially active substances. Preferred nonionic surfactants have proven to be alkyl polyglycosides together with alkylene oxide addition products onto fatty alcohols and fatty acids with in each case 2 to 30 mol of ethylene oxide per mol of fatty alcohol or fatty acid respectively. Preparations having excellent properties are likewise obtained if they include fatty acid esters of ethoxylated glycerol as the nonionic surfactants.

The nonionic, zwitterionic or amphoteric surfactants are used in proportions of 0.1 to 45 wt. %, preferably of 1 to 30 wt. % and particularly preferably of 1 to 15 wt. %, relative to the total quantity of the ready-to-use agents.

Agents which are suitable according to the invention may also include cationic surfactants of the quaternary ammonium compound, ester quat and amidoamine type. Preferred quaternary ammonium compounds are ammonium halides and the imidazolium compounds known under the INCI names Quaternium-27 and Quaternium-83. Quaternized protein hydrolysates are further cationic surfactants which are usable according to the invention. One compound from the amidoamines which is particularly suitable according to the invention is stearamidopropyldimethylamine which is commercially available under the name Tegoamidt S 18. Preferred ester quats are quaternized ester salts of fatty acids with triethanolamine, quaternized ester salts of fatty acids with diethanolalkylamines and quaternized ester salts of fatty acids with 1,2-dihydroxypropyldialkylamines. The cationic surfactants are present in the agents according to the invention preferably in proportions of from 0.05 to 10 wt. %, relative to the total agent.

The ready-to-use coloring agents may include further auxiliary substances and additives. It has for instance proven advantageous for the agent to include at least one thickener. No restrictions apply in principle with regard to these thickeners. Both organic and purely inorganic thickeners may be used.

Suitable thickeners are anionic, synthetic polymers; cationic, synthetic polymers; naturally occurring thickeners, such as nonionic guar gums, scleroglucan gums or xanthan gums, gum arabic, gum ghatti, karaya gum, tragacanth gum, carrageenan gum, agar-agar, locust bean flour, pectins, alginates, starch fractions and derivatives such as amylose, amylopectin and dextrins, and cellulose derivatives, such as for example methylcellulose, carboxyalkylcelluloses and hydroxyalkylcelluloses; nonionic, synthetic polymers such polyvinyl alcohol or polyvinylpyrrolidinone; as well as inorganic thickeners, in particular phyllosilicates such as for example bentonite, in particular smectites, such as montmorillonite or hectorite.

Coloring processes on keratin fibers conventionally proceed in an alkaline environment. Establishing an excessively high pH value is, however, not desirable if the keratin fibers and also the skin are to be treated as gently as possible. It is therefore preferred for the pH value of the ready-to-use agent to be between 6 and 11, in particular between 7 and 10.5. The pH values for the purposes of the present invention are pH values which were measured at a temperature of 22° C.

Alkalizing agents usable for adjusting the preferred pH according to the invention may be selected from the group which is formed by ammonia, alkanolamines, basic amino acids, and inorganic alkalizing agents such as alkali(ne earth) metal hydroxides, alkali(ne earth) metal metasilicates, alkali (ne earth) metal phosphates and alkali(ne earth) metal hydrogenphosphates. Preferred inorganic alkalizing agents are magnesium carbonate, sodium hydroxide, potassium hydroxide, sodium silicate and sodium metasilicate. Organic alkalizing agents usable according to the invention are preferably selected from monoethanolamine, 2-amino-2-methylpropanol and triethanolamine. The basic amino acids usable as alkalizing agents according to the invention are preferably selected from the group formed by arginine, lysine, ornithine and histidine, more preferably arginine.

It has furthermore proven advantageous for the coloring agents, in particular if they additionally include hydrogen peroxide, to include at least one stabilizer or complexing agent. More preferred stabilizers are phenacetin, alkali metal benzoates (sodium benzoate) and salicylic acid. Any prior art complexing agents may furthermore be used. Complexing agents which are preferred according to the invention are nitrogen-containing polycarboxylic acids, in particular EDTA and EDDS, and phosphonates, in particular 1-hydroxyethane-1,1-diphosphonate (HEDP) and/or ethylenediaminetetramethylenephosphonate (EDTMP) and/or diethylenetriaminepentamethylenephosphonate (DTPMP) or the sodium salts thereof.

The agents according to the invention may moreover include further active substances, auxiliary substances and additives, such as nonionic polymers (for example vinylpyrrolidinone/vinyl acrylate copolymers, polyvinylpyrrolidinone, vinylpyrrolidinone/vinyl acetate copolymers, polyethylene glycols and polysiloxanes); silicones, such as volatile or non-volatile, straight-chain, branched or cyclic, crosslinked or uncrosslinked polyalkylsiloxanes (such as dimethicones or cyclomethicones), polyarylsiloxanes and/or polyalkylarylsiloxanes, in particular polysiloxanes with organofunctional groups, such as substituted or unsubstituted amines (amodimethicones), carboxyl, alkoxy and/or hydroxyl groups (dimethicone copolyols), linear polysiloxane(A)-polyoxyalkylene(B) block copolymers, grafted silicone polymers); cationic polymers, such as quaternized cellulose ethers, polysiloxanes with quaternary groups, such as dimethyldiallylammonium chloride copolymers, dimethylaminoethylmethacrylate methosulfate-vinylpyrrolidinone copolymers quaternized with diethyl sulfate, vinylimidazolinium methochloride copolymers; zwitterionic and amphoteric polymers; anionic polymers such as for example polyacrylic acids or crosslinked polyacrylic acids; structuring agents such as glucose, maleic acid and lactic acid, hair-conditioning compounds, such as phospholipids, for example lecithin and cephalins; perfume oils, dimethyl isosorbide and cyclodextrins; active substances which improve fiber structure, in particular mono-, di- and oligosaccharides such as for example glucose, galactose, fructose, fruit sugar and lactose; dyes for coloring the agent; antidandruff active ingredients such as piroctone olamine, zinc omadine and climbazole; amino acids and oligopeptides; animal- or plant-based protein hydrolysates, as well as in the form of the fatty acid condensation products or optionally anionically or cationically modified derivatives thereof; vegetable oils; light stabilizers and UV blockers; active substances such as panthenol, pantothenic acid, pantolactone, allantoin, pyrrolidinone carboxylic acids and the salts thereof and bisabolol; polyphenols, in particular hydroxycinnamic acids, 6,7-dihydroxycoumarins, hydroxybenzoic acids, catechins, tannins, leucoanthocyanidines, anthocyanidines, flavanones, flavones and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogencarbonates, guanidines, ureas and primary, secondary and tertiary phosphates; opacifiers such as latex, styrene/PVP and styrene/acrylamide copolymers; pearlescent agents such as ethylene glycol mono- and distearate as well as PEG-3 distearate; pigments and propellants such as propane-butane mixtures, $N_2O$, dimethyl ether, $CO_2$ and air.

A person skilled in the art will select these further substances in accordance with the desired properties of the agents. With regard to further optional components and the quantities of these components used, reference is explicitly made to the relevant handbooks known to a person skilled in the art. The additional active substances and auxiliaries are preferably used in the agents according to the invention in quantities of in each case 0.0001 to 25 wt. %, in particular of 0.0005 to 15 wt. %, relative to the total weight of the mixture for use.

The sole use of hydrogen peroxide or the addition products thereof onto organic or inorganic compounds is often not sufficient for major lightening of very dark hair. The agents according to the invention may therefore additionally include still further blonding and/or bleaching agents.

If, in addition to coloring of the keratinic fibers, strong lightening is also desired, it therefore preferred according to the invention for a blonding preparation (C) including at least one bleach activator to be mixed with the mixture of oxidizing agent preparation (B) and preparation (A) including at least one oxidation dye precursor according to formula (I).

It may here be immaterial whether a mixture of (A) and (B) is firstly produced and then the blonding preparation (C) is mixed in, or whether the individual components are mixed in a different sequence. It is preferred to mix the individual preparations in as rapid a succession as possible and preferably to apply the ready-to-use agent promptly onto the keratinic fibers.

A further embodiment of the present application is therefore an agent for bleaching and coloring keratinic fibers which is characterized in that it is produced before use by mixing at least one oxidizing agent preparation (B) including at least one oxidizing agent selected from hydrogen peroxide and the addition compounds thereof onto solid carriers, at least one blonding preparation (C) including at least one bleach booster and at least one preparation (A) including in a cosmetic carrier at least one oxidation dye precursor according to formula (I).

As has already been mentioned, the agents according to the invention may also be produced immediately before use from two or more separately packaged preparations. This is in particular appropriate for separating incompatible ingredients in order to avoid a premature reaction. Separation into multicomponent systems is in particular appropriate where ingredient incompatibilities are to be expected or feared. In such systems, the ready-to-use agent is produced by the consumer immediately before use by mixing the components. A coloring and/or lightening agent in which the oxidation dye precursors are initially separate from the oxidizing agent preparation, preferably including hydrogen peroxide, is here preferred.

A preferred presentation of the agent according to the invention is a packaging unit (kit of parts) which, in containers separately packaged from one another, includes in a container A at least one preparation (A) including in a cosmetic carrier at least one oxidation dye precursor according to formula (I), and in a container B at least one oxidizing agent preparation (B) including in a cosmetic carrier at least one oxidizing agent.

If a particularly strong lightening effect is desired, a preferred further presentation of the agent according to the invention is a packaging unit (kit of parts) which, in containers separately packaged from one another, includes in a container A at least one preparation (A) including in a cosmetic carrier at least one oxidation dye precursor according to formula (I), in a container B at least one oxidizing agent preparation (B) including at least one oxidizing agent, and in a container C at least one blonding preparation (C) including at least one bleach booster.

The multicomponent packaging unit (kit of parts) additionally includes a set of instructions. It may furthermore be preferred for an application aid, such as for example a comb or a brush, and/or personal protective equipment, such as for example disposable gloves, also to be enclosed with the kit.

The above statements regarding the agents according to the invention apply mutatis mutandis with regard to further preferred embodiments of the multicomponent packaging unit (kit of parts).

The actual hair coloring agent is expediently produced immediately before use by mixing preparations (A) with (B) and optionally (C). Use temperatures may be in a range between 15 and 40° C. After a period of exposure of 5 to 45 minutes, the hair coloring agent is rinsed out of the hair to be dyed. Rewashing with a shampoo is not required if a carrier with an elevated surfactant content, e.g. a coloring shampoo, has been used.

The present invention accordingly also provides a method for coloring and optionally lightening human hair, in which an agent according to the invention as defined above is applied onto the hair, left on the hair for a period of exposure of 5 to 45 minutes, preferably of 8 to 35 minutes, and rinsed back out of the hair or washed out with a shampoo.

While the agent is acting on the fiber it may be advantageous to assist the dyeing process by supplying heat. Heat may be supplied by an external heat source, such as for example hot air from a hot air blower, and also, in particular when coloring the hair of a living test subject, by the body temperature of the test subject. In the case of the latter possibility, the part to be dyed is conventionally covered with a cap. In particular, the temperature during the period of exposure is between 10° C. and 45° C., in particular between 20° C. and 40° C. The coloring agents according to the invention produce intense colorings even at physiologically acceptable temperatures of below 45° C. They are therefore particularly suitable for coloring human hair.

The present invention also provides the use of an agent according to the invention in oxidative coloring agents for human hair for improving the gray coverage, equalization, color intensity, durability and/or colorfulness of the coloring results.

The above statements regarding the agents according to the invention apply mutatis mutandis with regard to further preferred embodiments of the methods and uses according to the invention.

The present invention finally provides compounds according to formula (I) of the first subject matter of the invention. The above statements regarding the agents according to the

SYNTHESIS EXAMPLES

Scheme I:

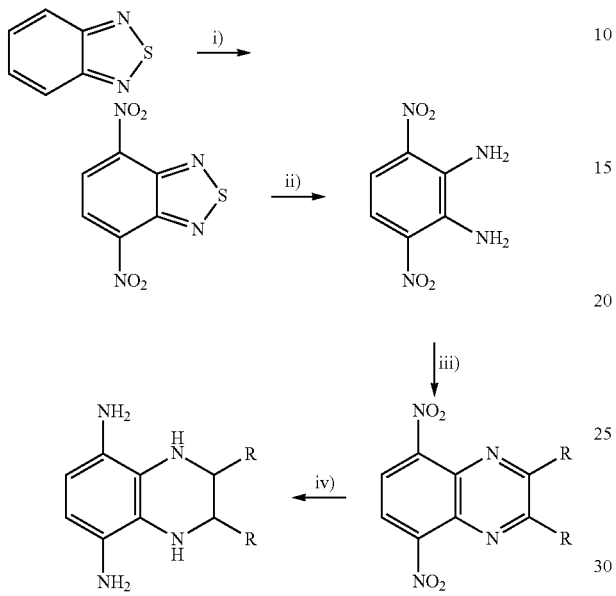

i) nitration; ii) reduction, for example NaBH$_4$; iii) anellation:
R—C(═O)—C(═O)—R;
iv) reduction, for example Raney nickel.

Scheme II:

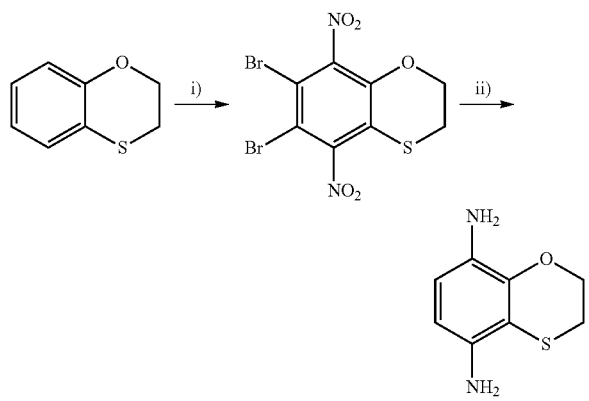

i) (a) bromination, for example Br$_2$/CH$_3$CO$_2$H; (b) nitration, for example HNO$_3$;
ii) reduction, for example H$_2$/Pd.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for oxidative color modification of keratinic fibers comprising in a cosmetic carrier, as an oxidation dye precursor of the developer type, at least one compound of formula (I)

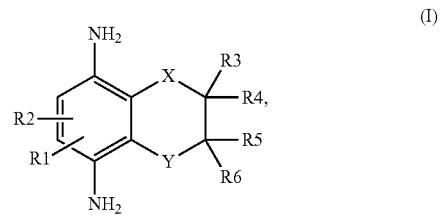

(I)

in which
R1 and R2 mutually independently denote a hydrogen atom, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom,
R3, R4, R5, R6 in each case mutually independently denote a hydrogen atom, a $C_1$-$C_6$ alkyl group, a $C_2$-$C_6$ alkenyl group, a $C_1$-$C_6$ hydroxyalkyl group, a $C_1$-$C_6$ alkoxy group, an amino group, a $C_1$-$C_6$ alkylamino group, a di($C_1$-$C_6$-alkyl)amino group, an N-(azacycloalkyl) group, an amino-($C_1$-$C_6$)-alkyl group, a $C_1$-$C_6$-alkylamino-$C_1$-$C_6$-alkyl group, a di-$C_1$-$C_6$-alkylamino-$C_1$-$C_6$-alkyl group, an N-(azacycloalkyl)-$C_1$-$C_6$-alkyl group, a $C_2$-$C_6$ polyhydroxyalkyl group, an acetoxy-$C_1$-$C_6$-alkyl group, a $C_1$-$C_6$-alkoxy-$C_1$-$C_6$-alkyl group, a carboxy-$C_1$-$C_6$-alkyl group or a halogen atom,
X denotes sulfur,
Y denotes oxygen, and
R7 dentoes a hydrogen atom, a $C_1$-$C_6$ alkyl group, a $C_2$-$C_6$ alkenyl group, a $C_1$-$C_6$ hydroxyalkyl group or a $C_2$-$C_6$ polyhydroxyalkyl group,
and/or the physiologically acceptable salt thereof.

2. The agent according to claim 1, wherein formula (I) is constituted such that the residues R3, R4, R5 or R6 in each case mutually independently denote a hydrogen atom, a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group.

3. The agent for oxidative color modification of keratinic fibers comprising in a cosmetic carrier, as an oxidation dye precursor of the developer type, at least one compound of formula(I)

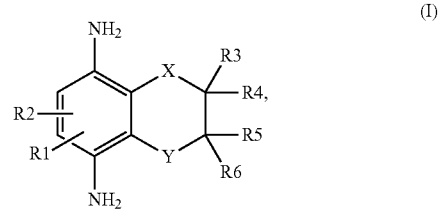

(I)

in which
R1 or R2 mutually independently denote a hydrogen atom, a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

R3, R4, R5, R6 in each case mutually independently denote a hydrogen atom, a $C_1$-$C_6$ alkyl group, a $C_2$-$C_6$ alkenyl group, a $C_1$-$C_6$ hydroxyalkyl group, a $C_1$-$C_6$ alkoxy group, an amino group, a $C_1$-$C_6$ alkylamino group, a di($C_1$-$C_6$alkyl)amino group, an N-(azacycloalkyl) group, an amino-($C_1$-$C_6$)-alkyl group, a $C_1$-$C_6$ alkylamino-$C_1$-$C_6$-alkyl group, a di-$C_{1\text{-}C6}$-alkylamino-$C_1$-$C_6$-alkyl group, an N-(azacycloalkyl)-$C_1$-$C_6$-alkyl group, a $C_2$-$C_6$ polyhydroxyalkyl group, an acetoxy-$C_1$-$C_6$-alkyl group, a $C_1$-$C_6$-alkoxy-$C_1$-$C_6$-alkyl group, a carboxy-$C_1$-$C_6$-alkyl group or a halogen atom, X and Y in each case mutually independently denote oxygen, sulfur, a group N—R7 or methylene, and R7 denotes a hydrogen atom, a $C_1$-$C_6$ alkyl group, a $C2$-$C_6$ alkenyl group, a $C_1$-$C_6$ hydroxyalkyl group or a $C_2$'$C_6$ polyhydroxyalkyl group, and/or the physiologically acceptable salt thereof,
with the proviso that if X and Y do not simultaneously denote oxygen at least one of the two residues R1 or R2 denotes a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom, and if X and Y in each case denote oxygen, R1 and R2 mutually independently denote hydrogen or methoxy and at least one of the residues R3, R4, R5 and/or R6 denotes a $C_1$'$C_6$-dialkylamino -$C_1$-$C_6$-alkyl group, a di($C_1$-$C_6$-alkyl)amino C 1-$C_6$-alkylgroup, or an N-(azacycloalkyl)-$C_1$-$C_6$-alkyl group.

4. The agent according to claim 1, wherein formula (I) is constituted such that one of the two residues R1 or R2 denotes hydrogen and the other residue R2 or R1 denotes a methoxy group.

5. The agent according to claim 1, wherein formula (I) is constituted such that the two residues R1 and R2 mutually independently denote a group which is selected from a $C_1$-$C_6$ alkyl group, a $C_2$-$C_6$ alkenyl group, a $C_1$-$C_6$ hydroxyalkyl group, a $C_2$-$C_6$ polyhydroxyalkyl group, a hydroxyl group, a $C_1$-$C_6$ alkoxy group or a halogen atom.

6. The agent according to claim 1, wherein formula (I) is constituted such that the two residues R1 and R2 denote a methoxy group.

7. The agent according to claim 1, wherein formula (I) is constituted such that exactly one of the residues R3, R4, R5 or R6 denotes a $C_1$-$C_6$ alkyl group, a $C_1$-$C_6$ alkoxy group, an amino group, a di($C_1$-$C_6$-alkyl)amino group, an N-(azacycloalkyl) group or a $C_1$-$C_6$-dialkylamino-$C_1$-$C_6$-alkyl group and the other three residues are hydrogen atoms.

8. An agenst for oxidative color modification of keratinic fibers comprising in a cosmetic carrier, as an oxidation dye precursor of the developer type, at least one compound selected from the group consisting of 2,3-dihydro-1,4-benzoxathiine-5,8-diamine, 2-methoxy-2,3-dihydro-1,4-benzoxathiine-5,8-diamine, 2-ethoxy-2,3-dihydro-1,4-benzoxathiine-5,8-diamine, $N^2,N^2$-dimethyl-2,3-dihydro-1,4-benzoxathiine-2,5,8-triamine, 2-[(dimethylamino)methyl]-2,3-dihydro-1,4-benzoxathiine-5,8-diamine, 3-methoxy-2,3-dihydro-1,4-benzoxathiine-5,8-diamine, $N^3,N^3$-dimethyl-2,3-dihydro-1,4-benzoxathiine-3,5,8-triamine, 3-[(dimethylamino)methyl]-2,3-dihydro-1,4-benzoxathiine-5,8-diamine, 1,2,3,4-tetrahydroquinoxaline-5,8-diamine, 2-methyl-1,2,3,4-tetrahydroquinoxaline-5,8-diamine, 2-methoxy-1,2,3,4-tetrahydroquinoxaline-5,8-diamine, 2-[(dimethylamino)methyl]-1,2,3,4-tetrahydroquinoxaline-5,8-diamine, 5-amino-7-methoxy-2,3-dihydro-1,4-benzoxathiin-8-ylamine, 2,7-dimethoxy-2,3-dihydro-1,4-benzoxathiine-5,8-diamine, 2-[(dimethylamino)methyl]-7-methoxy-2,3-dihydro-1,4-benzoxathiine-5,8-diamine, 3,7-dimethoxy-2,3-dihydro-1,4-benzoxathiine-5,8-diamine, 3-[(dimethylamino)methyl]-7-methoxy-2,3-dihydro-1,4-benzoxathiine-5,8-diamine, 7-methoxy-1,2,3,4-tetrahydroquinoxaline-5,8-diamine, 2,7-dimethoxy-1,2,3,4-tetrahydroquinoxaline-5,8-diamine, 2-[(dimethylamino)methyl]-7-methoxy-1,2,3,4-tetrahydroquinoxaline-5,8-diamine, 5-amino-6-methoxy-2-methyl-2,3-dihydro-1,4-benzoxathiin -8-ylamine, 5-amino-6-methoxy-2,3-dihydro-1,4-benzoxathiin-8-ylamine, 2,6-dimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6-dimethoxy-2,3-dihydro -1,4-benzoxathiine-5,8-diamine, 3-[(dimethylamino)methyl]-6-methoxy-2,3-dihydro-1,4-benzoxathiine-5,8-diamine, 2,6-dimethoxy-1,2,3,4-tetrahydroquinoxaline-5,8-diamine, 2-[(dimethylamino)methyl]-6-methoxy-1,2,3,4-tetrahydroquinoxaline-5,8-diamine, 5-amino-6,7-dimethoxy-2,3-dihydro-1,4-benzoxathiin-8-ylamine, 2,6,7-trimethoxy-2,3-dihydro-1,4-benzoxathiine-5,8-diamine, 2-[(dimethylamino)methyl]-6-methoxy-2,3-dihydro-1,4-benzoxathiine-5,8-diamine, 3,6,7-trimethoxy-2,3-dihydro-1,4-benzoxathiine-5,8-diamine, 3-[(dimethylamino)methyl]-6,7-dimethoxy-2,3-dihydro-1, 4-benzoxathiine-5,8-diamine, 6,7-dimethoxy-1,2,3,4-tetrahydroquinoxaline-5,8-diamine, 2,6,7-trimethoxy-1,2,3,4-tetrahydroquinoxaline-5,8-diamine, 2-[(dimethyl-amino)methyl]-6,7-dimethoxy-1,2,3,4-tetrahydroquinoxaline-5,8-diamine, 6,7-dimethoxy-(2-dimethylaminomethyl)-2,3-dihydro-1,4-benzodioxine-5,8-diamine, (2-dimethylamino)-2,3-dihydro-1,4-benzodioxine-5,8-diamine, and the physiologically acceptable salts thereof.

9. The agent according to claim 1, wherein the compound according to formula (I) is included in a proportion by weight of 0.001 to 10.0 wt. % relative to total weight of the ready-to-use agent.

10. The agent according to claim 1, further comprising at least one oxidation dye precursor of the coupler type which is selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethyl-amino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino-2-methylamino-6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline and the physiologically acceptable salts thereof.

11. A compound of formula (I) as set forth in claim 1.

12. The agent according to claim 3, wherein formula (I) is constituted such that X and Y do not simultaneously denote oxygen and one of the two residues R1 or R2 denotes hydrogen and the other residue R2 or R1 denotes a methoxy group.

13. The agent according to claim 3, wherein formula (I) is constituted such that X and Y do not simultaneously denote oxygen and the two residues R1 and R2 mutually independently denote a group which is selected from a $C_1$-$C_6$ alkyl group, a C2-$C_6$ alkenyl group, a $C_1$-$C_6$ hydroxyalkyl group, a C2-$C_6$ polyhydroxyalkyl group, a hydroxyl group, a $C_1$-$C_6$ alkoxy group or a halogen atom.

14. The agent according to claim 3, wherein formula (I) is constituted such that X and Y do not simultaneously denote oxygen and the two residues R1 and R2 denote a methoxy group.

15. The agent according to claim 3, wherein formula (I) is constituted such that X and Y do not simultaneously denote oxygen and exactly one of the residues R3, R4, R5 or R6 denotes a $C_1$-$C_6$ alkyl group, an amino group, a di($C_1$-$C_6$-alkyl)amino group, an N-(azacycloalkyl) group or a $C_1$-$C_6$-dialkylamino-$C_1$-$C_6$-alkyl group and the other three residues are hydrogen atoms.

16. The agent according to claim 3, wherein the compound according to formula (I) is included in a proportion by weight of 0.001 to 10.0 wt. % relative to total weight of the ready-to-use agent.

17. The agent according to claim 3, further comprising at least one oxidation dye precursor of the coupler type which is selected from the group consisting of 3-aminophenol, 5-amino-2-methylphenol, 3-amino-2-chloro-6-methylphenol, 2-hydroxy-4-aminophenoxyethanol, 5-amino-4-chloro-2-methylphenol, 5-(2-hydroxyethyl)-amino-2-methylphenol, 2,4-dichloro-3-aminophenol, 2-aminophenol, 3-phenylenediamine, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino)ethanol, 2-({3-[(2-hydroxyethyl)amino]-2-methoxy-5-methylphenyl}amino)ethanol, 2-({3-[(2-hydroxyethyl)amino]-4,5-dimethylphenyl}amino) ethanol, 2-[3-morpholin-4-yl -phenyl)amino]ethanol, 3-amino-4-(2-methoxyethoxy)-5-methylphenylamine, 1-amino-3-bis-(2-hydroxyethyl)aminobenzene, resorcinol, 2-methylresorcinol, 4-chlororesorcinol, 1,2,4-trihydroxybenzene, 2-amino-3-hydroxypyridine, 3-amino -2-methylamino -6-methoxypyridine, 2,6-dihydroxy-3,4-dimethylpyridine, 3,5-diamino-2,6-dimethoxypyridine, 1-phenyl-3-methylpyrazol-5-one, 1-naphthol, 1,5-dihydroxynaphthalene, 2,7-dihydroxynaphthalene, 1,7-dihydroxynaphthalene, 1,8-dihydroxynaphthalene, 4-hydroxyindole, 6-hydroxyindole, 7-hydroxyindole, 4-hydroxyindoline, 6-hydroxyindoline, 7-hydroxyindoline and the physiologically acceptable salts thereof.

18. A compound of formula (I) as set forth in claim 3.

* * * * *